(12) United States Patent
Izmailov et al.

(10) Patent No.: US 10,946,375 B2
(45) Date of Patent: Mar. 16, 2021

(54) DISPOSABLE BIOASSAY CARTRIDGE AND METHOD OF PERFORMING MULTIPLE ASSAY STEPS AND FLUID TRANSFER WITHIN THE CARTRIDGE

(71) Applicant: AXELA INC., Etobicoke (CA)

(72) Inventors: Alexandre Izmailov, Etobicoke (CA); David Englert, West Hartford, CT (US); Paul Smith, Acton (CA)

(73) Assignee: Angle Europe Limited, Guildford (GB)

( * ) Notice: Subject to any disclaimer, the term of this patent is extended or adjusted under 35 U.S.C. 154(b) by 153 days.

(21) Appl. No.: 15/564,791

(22) PCT Filed: Apr. 11, 2016

(86) PCT No.: PCT/CA2016/050414
§ 371 (c)(1),
(2) Date: Oct. 6, 2017

(87) PCT Pub. No.: WO2016/161524
PCT Pub. Date: Oct. 13, 2016

(65) Prior Publication Data
US 2018/0117582 A1    May 3, 2018

Related U.S. Application Data

(60) Provisional application No. 62/165,347, filed on May 22, 2015, provisional application No. 62/214,330, filed on Apr. 9, 2015.

(51) Int. Cl.
*B01L 3/00* (2006.01)
*C12M 1/00* (2006.01)
(Continued)

(52) U.S. Cl.
CPC .......... *B01L 3/502* (2013.01); *B01L 3/50273* (2013.01); *B01L 7/52* (2013.01); *C12M 23/28* (2013.01);
(Continued)

(58) Field of Classification Search
None
See application file for complete search history.

(56) References Cited

U.S. PATENT DOCUMENTS 4,756,884 A * 7/1988 Hillman ................ B01F 5/0618
366/DIG. 3
5,458,852 A * 10/1995 Buechler .............. B01J 19/0093
422/417
(Continued)

FOREIGN PATENT DOCUMENTS

EP      1203959 A1    5/2002
JP      2003166910    6/2003
(Continued)

OTHER PUBLICATIONS

International Search Report for PCT/CA2016/050414 dated Jul. 29, 2016.
(Continued)

*Primary Examiner* — Matthew D Krcha
(74) *Attorney, Agent, or Firm* — Hill & Schumacher

(57) ABSTRACT

The present disclosure provides a cartridge and method to move fluids within the cartridge that simplifies the design and removes the need for any internal valves or metering devices. The design is amenable to injection molded manufacturing lowering cost for large volume manufacturing. The design can be adapted to carry out both sample preparation and detection of biological substances including nucleic acids and proteins.

37 Claims, 25 Drawing Sheets

(51) Int. Cl.
*C12M 1/12* (2006.01)
*C12M 1/34* (2006.01)
*B01L 7/00* (2006.01)

(52) U.S. Cl.
CPC ............ *C12M 25/14* (2013.01); *C12M 41/40* (2013.01); *B01L 2200/025* (2013.01); *B01L 2200/026* (2013.01); *B01L 2200/0621* (2013.01); *B01L 2200/0684* (2013.01); *B01L 2200/0689* (2013.01); *B01L 2200/147* (2013.01); *B01L 2200/16* (2013.01); *B01L 2300/0681* (2013.01); *B01L 2300/0874* (2013.01); *B01L 2400/0406* (2013.01); *B01L 2400/0487* (2013.01); *B01L 2400/0683* (2013.01); *B01L 2400/084* (2013.01)

(56) References Cited

U.S. PATENT DOCUMENTS

| | | | |
|---|---|---|---|
| 5,716,842 A * | 2/1998 | Baier | B01J 19/0093 422/109 |
| 6,296,020 B1 | 10/2001 | McNeely et al. | |
| 6,383,748 B1 | 5/2002 | Carpay et al. | |
| 6,418,968 B1 | 7/2002 | Pezzuto et al. | |
| 6,635,493 B2 | 10/2003 | Van Damme et al. | |
| 6,770,322 B1 | 8/2004 | Moles | |
| 6,806,543 B2 | 10/2004 | Yamakawa et al. | |
| 6,849,408 B2 | 2/2005 | Carpay et al. | |
| 6,886,409 B2 | 5/2005 | Carpay | |
| 7,163,660 B2 | 1/2007 | Lehmann | |
| 7,192,510 B2 | 3/2007 | Den et al. | |
| 7,241,421 B2 | 7/2007 | Webster et al. | |
| 7,326,561 B2 | 2/2008 | Goodman et al. | |
| 8,551,422 B2 | 10/2013 | Wan et al. | |
| 2002/0023684 A1* | 2/2002 | Chow | B01J 19/0093 137/833 |
| 2004/0042930 A1 | 3/2004 | Clemens et al. | |
| 2004/0053422 A1* | 3/2004 | Chan | B01D 61/022 436/180 |
| 2004/0142463 A1* | 7/2004 | Walker | A61M 1/36 435/325 |
| 2006/0014198 A1* | 1/2006 | Dertinger | B01L 3/5023 435/6.19 |
| 2007/0184494 A1* | 8/2007 | McBride | B01D 61/00 435/7.9 |
| 2011/0143339 A1* | 6/2011 | Wisniewski | B01L 3/5023 435/6.1 |
| 2012/0037591 A1 | 2/2012 | Tringe et al. | |
| 2013/0032235 A1 | 2/2013 | Johnstone et al. | |

FOREIGN PATENT DOCUMENTS

| | | |
|---|---|---|
| JP | 2006149215 | 6/2006 |
| JP | 2006162592 | 6/2006 |
| JP | 2007097444 | 4/2007 |
| JP | 2007520692 | 7/2007 |
| JP | 2009500602 | 1/2009 |
| JP | 2014417909 | 7/2014 |
| JP | 2014517909 | 7/2014 |
| WO | 00/60352 | 10/2000 |
| WO | 0230561 | 4/2002 |
| WO | 03089931 | 10/2003 |
| WO | 2014182847 | 11/2014 |
| WO | 2015015178 | 2/2015 |

OTHER PUBLICATIONS

Chen et Al, "Manually Operatable On-Chip Bistable Pneumatic Microstructures for Microfluididic Manipulations" . Lab on a Chip, Sep. 7, 2014 (Sep. 7, 2014), vol. 14(17), pp. 3401-3408, [online] [retrieved on Jul. 18, 2016 (Jul. 18, 2016)].

Kim et Al, "A microfluidic device for high throughput bacterial biotilm studies". Lab on a Chip, Mar. 21, 2012 (Mar. 21, 2012), vol. 12(6), pp. 1157-1163, [online] [retrieved on Jul. 18, 2016 (Jul. 18, 2016)].

Hosokawa et Al, "Handling of Picoliter Liquid Samples in a Poly (dimethylsiloxane)-Based Microfluidic Device". Analytical Chemistry, Oct. 15, 1999 (Oct. 15, 1999), vol. 71(20), pp. 4781-4781, [online] [retrieved on Jul. 18, 2016 (Jul. 18, 2016)].

Zhang et Al, "An all-in-one microfluidic device for parallel DNA extraction and gene analysis". Biomedical Microdevices, vol. 12(6), pp. 1043-1049, [online] [retrieved on Jul. 18, 2016 (Jul. 18, 2016)1.

* cited by examiner

201. Dissolution Buffer Chamber
202. Dried Reagent Chamber 3
203. Dried Reagent Chamber 2
204. Dried Reagent Chamber 1
205. Bulk Buffer Chamber 1
206. Enzyme Buffer
207. Bulk Buffer Chamber 2
208. Sample Chamber
209. Processing Chamber 1
210. Sample Pretreatment/Lysis Buffer Chamber
211. Thermal Treatment Chamber 1
212. Intermediate Chamber 1
213. Dried Reagent Chamber 4
214. Thermal Treatment Chamber 2
215. Thermal Insulating Zone
216. Thermal Treatment Chamber 3
217. Blocking Buffer Chamber
218. Intermediate Chamber 2
219. Hybridization Buffer Chamber 1
220. Detection Reagent Chamber
221. Imaging Reagent Chamber
222. Bulk Buffer Chamber 4
223. Hybridization Buffer Chamber 2
224. Processing Chamber 1
225. Bulk Buffer Chamber 3
226. Waste Chamber 1
227. Waste Chamber 2
228. Decontamination Chamber

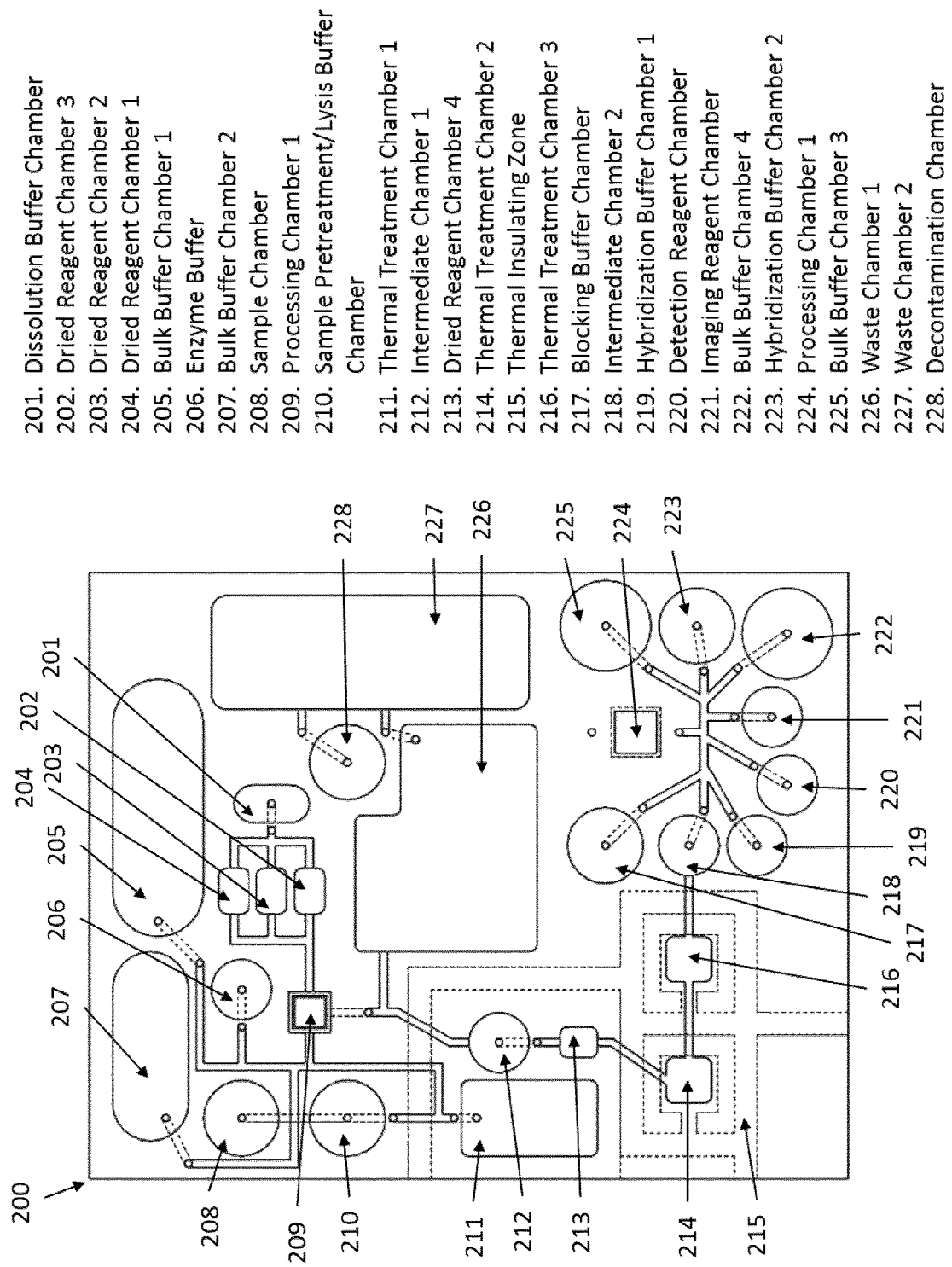

Figure 8

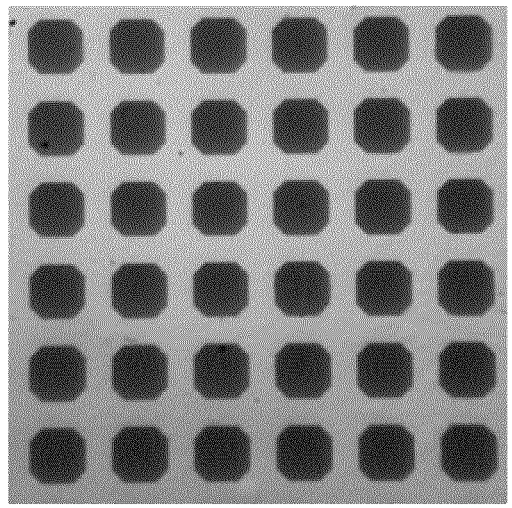
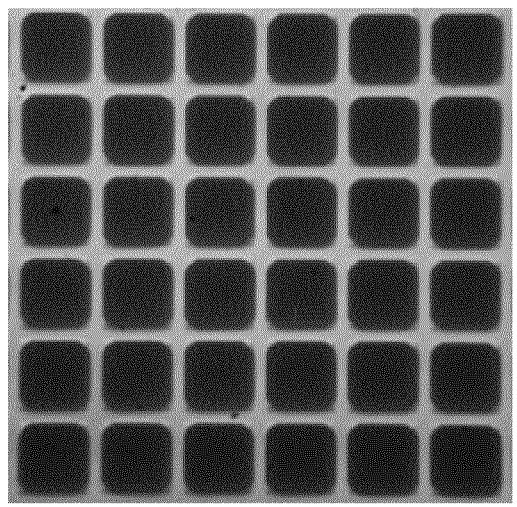
Figure 12

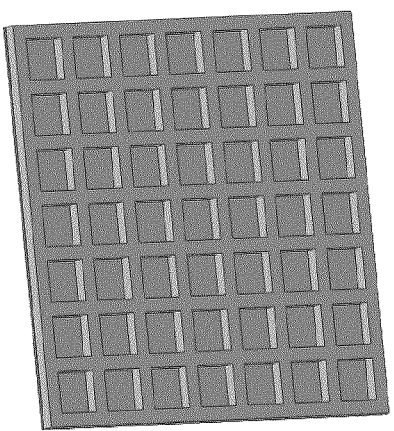
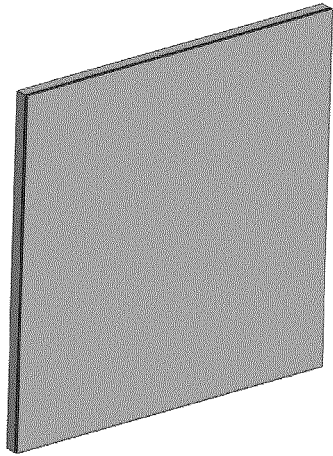
Figure 23

DISPOSABLE BIOASSAY CARTRIDGE AND METHOD OF PERFORMING MULTIPLE ASSAY STEPS AND FLUID TRANSFER WITHIN THE CARTRIDGE

FIELD

The present disclosure relates to a disposable cartridge and method to move fluids and carry out multiple bioassay steps within the cartridge that simplifies the design and removes the need for any internal valves or metering devices. The design is amenable to injection molded manufacturing lowering cost for large volume manufacturing.

BACKGROUND

Typical cartridge devices for biological assays are interfaced with an instrument containing syringes or other types of positive displacement pumps in order to accurately meter liquid volumes required sequentially in a reaction zone within the disposable cartridge. This often also involves the integration of mechanical valves within the cartridge structure to control fluid flows. In addition, care must be taken in the design of the fluidic paths to eliminate the formation of air bubbles that can significantly interfere with accurate fluid transfer. Complex structures or bubble control mechanisms are introduced into the design to mitigate these issues. This introduces manufacturing complexity and increased cost of the cartridges which are often meant to be used in a disposable fashion.

In view the trend toward point of use diagnostic testing, there is a need to integrate multiple functions/assay steps in a single cartridge on a cost effective basis consistent with mass production of the disposable cartridges. Therefore, it would be very beneficial to provide a disposable cartridge which integrates multiple functions with a minimum number of moving parts such as active pumps and valves in the field of automated point of use diagnostic bioassays.

SUMMARY

The present invention is directed to device and method to transfer liquid volumes sequentially to a reaction zone with only the use of applied pressure or vacuum and does not require any internal valves. Fluidic transfer is limited within the cartridge by capillary pressures. Flow between reaction zones may be effected by switching pressure or vacuum between ports with external valves and hence selectively exceeding the capillary pressure in the elements of the cartridge connecting reaction zones. The pressure/vacuum source and valves are located in the instrument itself and are isolated from reaction fluids. None of these components are part of the disposable cartridge, significantly lowering complexity and cost.

In an embodiment there is provided a disposable sample handling cartridge for performing multiplex biological assays, comprising:

a) an upper processing chamber having a preselected volume and having a pneumatic port mounted on a top of the upper processing chamber;

b) a lower processing chamber located below said upper processing chamber and having a pneumatic port mounted on a top of the lower processing chamber;

c) a porous substrate positioned to separate the upper processing chamber from the bottom processing chamber with the porous substrate forming the bottom of the upper processing chamber wherein the porous substrate is connected to a body of the upper processing chamber in such a way that fluids can only exit through the bottom of the upper processing chamber into lower processing chamber by passing through the porous substrate when an applied pressure differential across the porous substrate exceeds a critical pressure;

d) one or more reagent reservoirs being in flow communication with said upper processing chamber by capillary channels configured to terminate in a top of the upper processing chamber such that they are located above a level of liquid in the upper processing chamber while performing assays, each reagent reservoir including at least one pneumatic port located on a top of the reservoir, a volume of the upper processing chamber being selected to be greater than a liquid volume to provide a head space in an upper portion of the upper processing chamber into which the capillary channels terminate;

e) an additional chamber in flow communication with said lower processing chamber by a capillary channel terminating in a top of the additional chamber, said addition chamber including a pneumatic port mounted on a top of the additional chamber; and wherein transport of liquids between selected chambers are controlled by application of pneumatic pressures with magnitudes required to overcome capillary pressure resistance between chambers.

In an embodiment there is provided a method for a performing biological assay, comprising:

providing a disposable sample handling cartridge having at least one set of processing chambers with each set of processing chambers including an upper processing chamber and a lower processing chamber separated by a porous substrate, the porous substrate being constructed of material containing pores selected to provide a uniform resistance to flow across its entire surface such that at a defined pressure differential across the porous substrate, liquids will pass through the pores but gases will not, the porous substrate having analyte specific receptors bound in said pores;

applying a differential pressure between one or more reagent chambers and a sample chamber containing an analyte and the upper processing chamber for moving liquids containing reagents and/or from one or more reagent chambers and sample chamber through capillary channels to the upper processing chamber;

applying a differential pressure between the upper processing chamber and the lower processing chamber for moving the liquids through the porous substrate from the upper processing chamber to the lower processing chamber with the differential pressure being selected to force the liquid through the porous substrate but not gas;

detecting for analytes bound to the analyte specific receptors on the porous substrate; and applying a differential pressure between the lower processing chamber and a waste chamber for moving liquids from the lower processing chamber to the waste chamber.

The present disclosure provides a porous substrate for detection of surface bound substances, comprising:

a generally planar microporous substrate material having opposed surfaces and pores extending through a thickness of said substrate in which the pores are wider near one surface of the substrate compared to a width of the pores on the opposed surface thereby improving the collection efficiency of light emitted from optical probes bound to the interior surfaces of the widened pores.

The pores may be progressively wider near one surface of the substrate.

The device, method disclosed herein is of particular use in the area of medical diagnostics (human and veterinary), food safety testing, monitoring of environmental and biological hazards and general measurement of biological species. The design can be adapted to carry out most common assay formats for both proteins and nucleic acids including sample preparation steps.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the drawings, in which:

FIG. 8 shows a top view of a cartridge configured for both nucleic acid sample preparation and nucleic acid amplification (isothermal or polymerase chain reaction (PCR)) and multiplex detection of the products.

FIGS. 12(a) and 12(b) show optical microphotographs of the front and back surfaces of a silicon substrate with tapered pores according to the present disclosure. These optical micrographs show that the high porosity of the substrate on the side with widened pores (FIG. 12(a)) and the lower porosity of the substrate on the opposite side (FIG. 12(b)).

FIG. 18 confirms the expected 40% improvement of light collection efficiency according to disclosure.

FIG. 23 shows an embodiment of the flow-through chip substrate with the high-efficiency porous substrate on the left hand side reinforced by a frame for structural stability, shown on the right hand side of the figure.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

Figure 1:
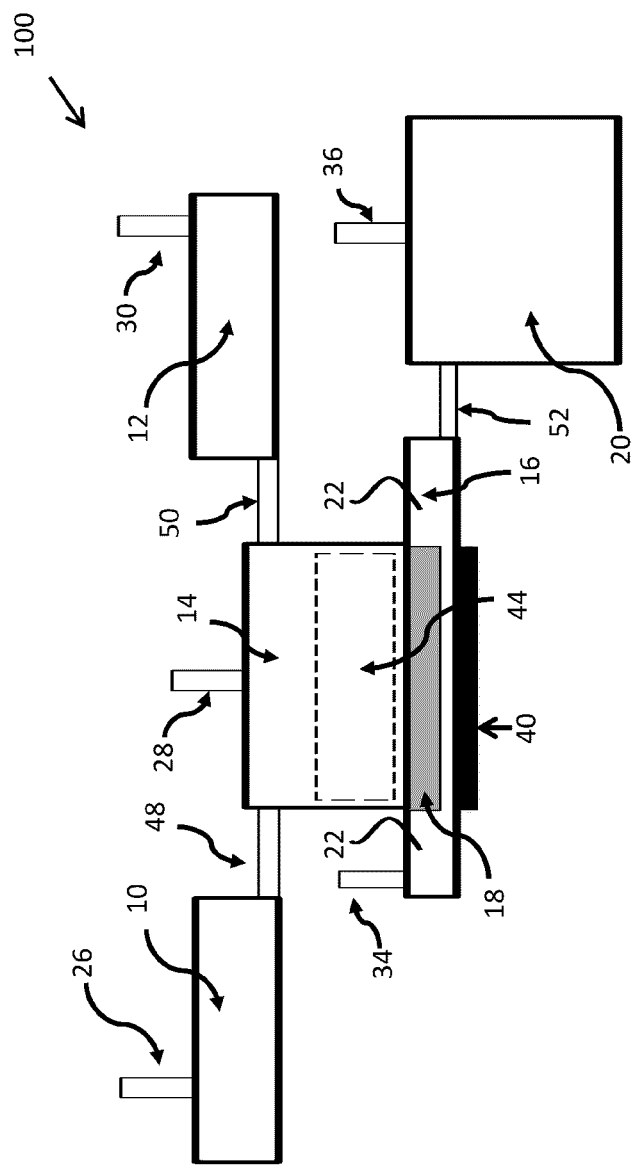
FIG. 1 is a side elevational view of a pneumatically driven assay cartridge showing the core components.

Referring to FIG. 1, there is shown a cartridge 100 configured to facilitate movement of fluids without the need for any internal valves or metering devices. The design is amenable to injection molded manufacturing lowering cost for large volume manufacturing. Cartridge 100 includes a first reagent chamber 10 which holds a liquid reagent or sample, and a second reagent chamber 12 which holds a second liquid reagent.

An upper processing chamber 14 is provided having a volume greater than first reagent chamber 10 or second reagent chamber 12. Cartridge 100 includes a lower processing chamber 16 which has a volume equal to or exceeding the maximum liquid capacity of upper processing chamber 14 and is designed to minimize the space between the bottom inner surface of chamber 16 and the bottom surface of a porous substrate 18 located within chamber 16. Cartridge 100 includes an outlet chamber 20 with a volume greater than all of the reagents and samples combined.

First reaction chamber 10 includes a pneumatic port 26 which is configured to provide negative differential pressure, positive differential pressure or vent under external system control to chamber 10. Upper processing chamber 14 includes a pneumatic port 28 which is configured to provide negative differential pressure, positive differential pressure or vent under external system control to upper processing chamber 14. Second reaction chamber 12 includes a pneumatic port 30 which is configured to provide negative differential pressure, positive differential pressure or vent under external system control to chamber 12. Lower processing chamber 16 includes a pneumatic port 34 which is configured to provide negative differential pressure, positive differential pressure or vent under external system control to lower processing chamber 16. Similarly, outlet chamber 20 includes a pneumatic port 36 configured to provide negative differential pressure, positive differential pressure or vent under external system control to outlet chamber 20.

Pneumatic ports 26, 28, 30, 34 and 36 may incorporate flexible diaphragms in their respective pneumatic conduits which can be used to isolate a given chamber from a pneumatic source while allowing a flux of gas through the conduit which is limited by the deformation of the diaphragm. Upon application of pneumatic pressure, gas will flow through the conduit until the back-pressure of the diaphragm equals the applied pneumatic pressure. Such flexible diaphragms are disclosed in U.S. Pat. No. 7,470,546, which is incorporated herein by reference in its entirety.

More particularly, flexible diaphragms may be incorporated into pneumatic ports 28 and 34 in FIG. 1 so that when a positive pneumatic pressure is applied to port 28 gas flows into upper processing chamber 14 until the diaphragm deforms enough to create a back pressure equal to the applied pressure. The gas entering the upper processing chamber 14 causes the liquid to flow through the porous substrate 18 into lower processing chamber 16, and air flows through port 34 and deforms the diaphragm in port 34 which would be vented to the atmosphere. Although port 34 is vented to the atmosphere there would be no passage of material between the interior of the cartridge 100 and the environment. This configuration permits back-and-forth transport of liquid across the porous substrate 18 by the periodic application of pressure to port 28 which can be vented to the atmosphere when pressure is not applied.

The porous substrate 18 serves as an interface between processing chambers 14 and 16 and has a size and shape configured to prevent fluid from passing between processing chambers 14 and 16 other than through the porous substrate 18 when the critical pressure is exceeded. Head spaces 22 are produced in lower processing chamber 16 due to porous substrate 18 projecting into lower processing chamber 16. While FIG. 1 shows two (2) head spaces 22 it will be understood that the cartridge may be configured to have only one. The direction of flow depends on the sign of the differential pressure between chambers 14 and 16.

Lower processing chamber 16 includes an optical window 40 which forms part of the lower surface of this lower processing chamber 16 to allow imaging of the porous substrate 18 from outside the device cartridge 100. In those embodiments using porous substrate 18 which has been functionalized with binding agents and which imaging is to be performed through optical window 40, porous substrate 18 is a rigid substrate disposed in a rigid plane parallel to the image plane of the imaging device such that it does not move or is not displaced which would result in poor quality images being detected. Preferred properties and structure of rigid porous substrate 18 will be discussed hereinafter.

Upper process chamber 14 includes a solid support zone 44 which is the space immediately above the porous substrate 18 which can be occupied by a solid support material of a larger size than the pores in the porous substrate 18 such that the material is retained in zone 44 since it cannot pass through the porous substrate 18. The support material is capable of binding analytes of interest or acting as a support for reactions between bound and soluble materials.

A capillary flow channel 48 connects reagent chamber 10 with the upper processing chamber 14 and is designed with an inner diameter sized to prevent flow in either direction until a differential pressure is applied exceeding a preselected critical level to permit flow between the chambers 10 and 14. A capillary flow channel 50 connects reagent chamber 12 with the upper processing chamber 14 and is designed with an inner diameter sized to prevent flow in either direction until a preselected differential pressure is applied exceeding the critical level to permit flow between the chambers 12 and 14. A capillary flow channel 52 connects lower processing chamber 16 with the outlet chamber 20 and is designed with an inner diameter sized to prevent flow in either direction until a preselected differential pressure is applied exceeding the critical level to permit flow. For example, the capillary inner diameter could be selected from the range of 50 to 500 microns to provide critical pressures of 0.1 to 0.5 psi.

Flow is effected from one chamber to the next by applying pressure to the originating chamber containing the fluid through the pneumatic port mounted on that chamber while simultaneously venting the destination chamber to which the capillary channel is connected through the pneumatic port mounted on that chamber. Alternatively, negative differential pressure can be applied to the destination chamber while simultaneously venting the originating chamber. In both cases a sufficient pressure differential must be provided to overcome the resistance of the channel and allow flow to occur.

In the case when a cycling of the fluid is required between two reagent chambers (e.g. for mixing) the differential pressure between these chambers can be changed from positive to negative and back to positive. This will change the direction of fluid flow.

Reagent chambers 10 and 12 may contain liquid reagents or dried reagents for dissolution in the device by transferring a solution from another chamber. One or more of the reagent chambers 10 and 12 may be designed to accept the introduction of a sample or other material from an external source. It is noted that while only two (2) reagent chambers 10 and 12 are shown connected to upper processing chamber 14, more could be included depending on the application at hand. Each reagent chamber 10 and 12 is provided with the port 26 for chamber 10 and port 30 for chamber 12 which can be interfaced with an external pneumatic system capable of providing one or more of positive or negative pressures or venting to a given chamber under external control.

The upper processing chamber 14 is provided with port 28 which can also be interfaced with an external pneumatic system capable of providing one or more of positive or negative pressures or venting to the chamber under external control.

The internal diameter of each capillary channel 48, 50 and 52 is selected to only permit flow through the channel from one chamber to the other when a differential pressure exceeding the critical pressure is applied. The length of the of the channel may be designed in the range of 5 to 30 mm in combination with the selected inner diameter in order to control the time required to transfer the full reagent volume between chambers in 1 to 60 seconds using applied pressures in the range of 0.1 to 1.5 psi. The internal diameter of each capillary channel 48, 50 and 52 can be constant along the channel. Alternatively, a part of the channel 48, 50 and 52 may have a smaller diameter (e.g. 50-500 um) and the rest of the channel may have a larger diameter (e.g. 500 um-2 mm). This type of channels 48, 50 and 52 allow independent selection of the critical pressure and flow rate.

The upper processing chamber 14 is sized to exceed the total volume of reagents or sample fluids that may be transferred to the upper processing chamber 14 at any time. As seen in FIG. 1, capillary channel 48 connecting reagent chamber 10 to upper processing chamber 14 and capillary channel 50 connecting reagent chamber 12 to upper processing chamber 14 are positioned so that they terminate in the upper portion of the upper processing chamber 14 such that all are above the maximum level of liquid reached in the chamber. The bottom of the upper processing chamber 14 is composed of the porous substrate 18 connected to the body of the chamber 14 in such a way that fluids can only exit through the bottom of the chamber 14 by passing through the porous substrate 18 when the differential pressure exceeds the critical pressure.

The upper processing chamber 14 may also contain the solid support 44 in the form of beads, particles, gels, or other similar materials that are capable of binding materials of interest from fluids within the chamber or acting as a support for bound materials to interact with materials contained in the fluid. These solid support materials 44 are of sufficient size that they are retained by the porous substrate 18 and do not restrict flow through the substrate 18.

The porous substrate 18 may also be composed of a material or modified in such a way as to act as a solid support capable of binding materials of interest from fluids that pass between the upper processing chamber 14 and the lower processing chamber 16 or acting as a support for bound materials to interact with materials contained in the fluid.

The porous substrate 18 is constructed of material containing pores selected to provide a uniform resistance to flow across its entire surface such that at a defined pressure differential across the substrate 18, fluids will pass through the pores but gases (e.g., air) will not. The properties of the pores are selected such that the resistance to flow will not be overcome by the weight of liquids in the upper processing chamber 14 or allow capillary action to draw fluids completely through the pores in substrate 18. The properties of the porous substrate 18 may optionally be selected to require a pressure differential to initiate flow that is in the same range as that required to initiate flow through capillaries 48, 50 and 52 in order to simplify design of the external pneumatic system. Flow between the upper processing chamber 14 and the lower processing chamber 16 is effected by applying pressure to the upper processing chamber 14 containing the fluid while simultaneously venting the lower processing chamber 16 separated by the porous substrate 18.

Alternatively, negative pressure can be applied to the lower chamber 16 while simultaneously venting the upper chamber 14. In both cases the pressure differential must be provided in a range that is sufficient to overcome the resistance of the pores in the substrate 18 and allow flow of liquids to occur but below that required to overcome the resistance to the flow of air through the pores. The process may be reversed to effect flow in the opposite direction to allow repeated contact with the substrate 18 and any solid support 44 contained in the upper chamber 14 as well as to provide efficient mixing.

The lower processing chamber 16 is provided with two or more ports 34 (only one is shown in FIG. 1) which can be interfaced with an external pneumatic system capable of providing one or more of positive or negative pressures or venting to the chamber 16 under external control. The lower processing chamber 16 has a volume equal to or greater than the maximum volume of reagents or sample fluids that may be transferred from the chamber 16 at any time.

The base of the lower processing chamber 16 is positioned in close proximity to the lower surface of the porous substrate 18 while additional volume can be provided by extending a portion of the chamber 16 laterally beyond the outer walls of the upper processing chamber 14 to form a headspace 22 in lower processing chamber 16.

The lower surface of the lower processing chamber 16 which includes the optically transparent window 40 which allows for imaging of the lower surface of the porous substrate 18 using for example a charge coupled device (CCD) camera or other suitable optical sensor.

The lower processing chamber 16 is connected to one or more outlet chambers 20 by one or more capillary channels 52 extending from the lowest point of the lower processing chamber 16 and terminating in the upper section of the outlet chamber 20 at a point above the maximum level of liquid to be contained in the outlet chamber 20. At least one of these capillary channels 52 is positioned at the lowest level of the chamber 16 to allow substantially all of the liquid in the chamber 16 to be removed through channel 52.

One outlet chamber 20 may be used for waste containment in which case it is sized with a volume greater than the sum of all the fluids that need to be transferred from the lower processing chamber 16. Another outlet chamber (not shown) may be used to transfer fluids to additional downstream chambers for further processing, depending on the tests to be performed.

In addition to controlling the flow of the fluid, the porous substrate 18 alone or in combination with the solid support 44 may be used to bind components in the fluid, and the bound components may be separated from the bulk fluid, washed, modified or copied, serve as binding agents for additional components, recovered for further use or any combination of these steps by the sequential transport of at least one fluid from a chamber on the device.

In addition to controlling the flow of the fluid, the porous substrate 18 may be designed to bind different substances in the fluid at different regions of the substrate 18, substances bound at different regions of the substrate 18 are subsequently detected and/or quantified.

A single device 100 may contain one or more processing zones (two are shown as processing chambers 14 and 16 but more could be included) which uses it's integral porous substrate 18 to accomplish different functions including analyte capture (nucleic acid, protein, small molecule other biological or chemical entities), modification of captured analyte (replication, extension, amplification, labeling, cleavage, hydrolysis), modification of soluble analytes through immobilized enzymes or catalysts, retention of solid matrix for higher capacity capture (beads, particles, gels), detection and/or quantitation of one or more captured analytes through optical imaging (colorimetric, fluorescent, chemiluminescent, bioluminescent). In all cases the porous substrate 18 also acts as a fluid control device necessary to carry out these functions.

The side views of FIGS. 2 to 6 show side views of an actual cartridge produced using plastic in which a central plastic cartridge reagent plate 82 is sandwiched between an upper cartridge plate 80 and a lower cartridge plate 84. FIG. 7 shows a photograph of an assembled cartridge and FIGS. 2 to 6 may be considered cross sections taken from FIG. 7.

Figure 2:
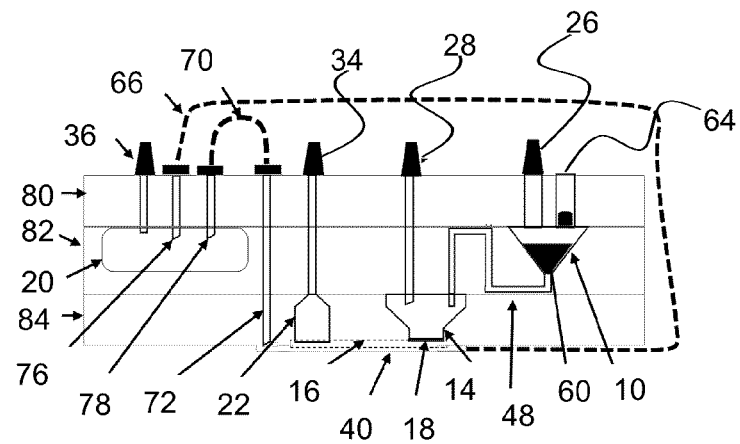
FIG. 2 shows a more detailed side view of the cartridge of FIG. 1 with liquids in the starting position.
Figure 3:
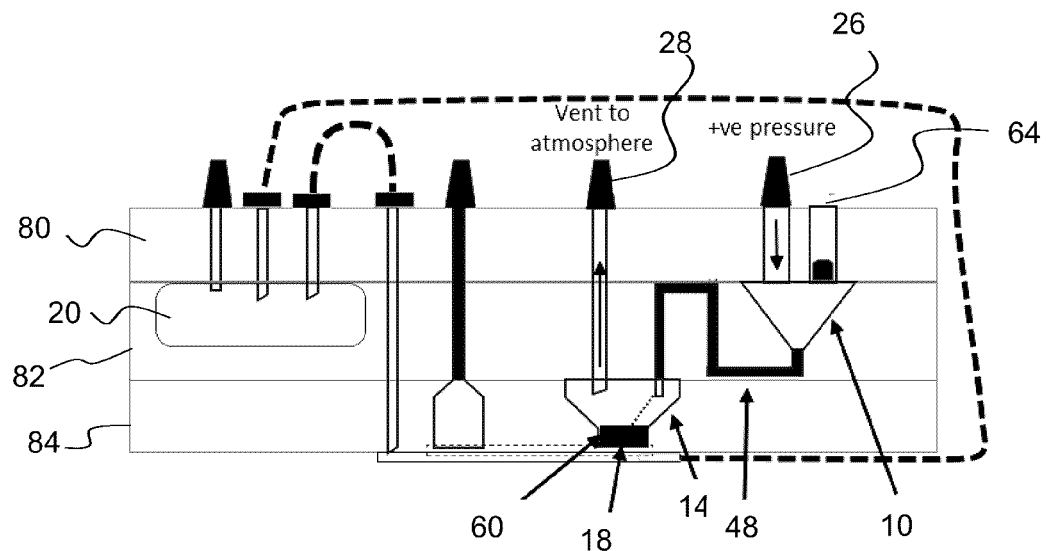
FIG. 3 is an enlarged view of the side view of FIG. 2 showing movement of the liquid (thick dark line within the capillary) from a reagent reservoir to an upper processing chamber under pneumatic control.

FIGS. 2 and 3 illustrate the dispensing of a liquid reagent or sample into the upper processing chamber 14. The liquid reagent or sample 60 is loaded into the reagent chamber 10 prior to the assay through a reagent/sample entry port 64 and then the port 64 is closed. A pressure of ~1 psi is applied to the chamber 10 containing the liquid 60 via port 26 while port 28 connected to the upper processing chamber 14 is vented creating a pressure differential allowing the reagent to flow through the reagent capillary channel 48 into upper processing chamber 14. The liquid 60 falls to the bottom of the upper processing chamber 14 and covers the integral porous substrate 18. Any excess air is allowed to vent through port 28. This method of dispensing fluids is similar for all other reagent chambers used in the assay, with the exception of a bulk wash buffer (not shown) which is stored in a larger reservoir and metered through a capillary channel on a timed basis so that a precise volume can be delivered during dispensing.

Figure 4:
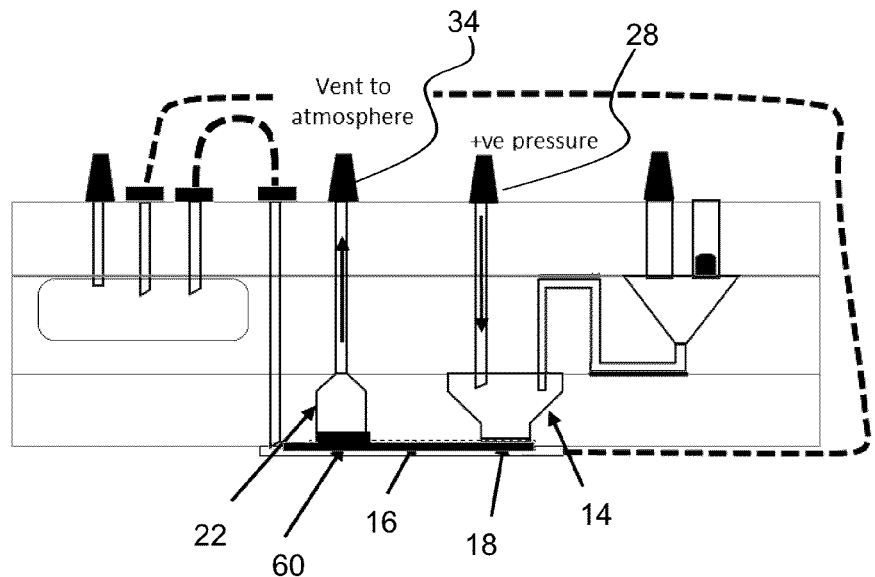
FIG. 4 is similar to FIG. 3 showing movement of the liquid from the upper processing chamber to a lower processing chamber through a porous substrate under pneumatic control.

Referring to FIG. 4, to pull the fluid through the porous substrate 18, a differential pressure is created by applying pressure through port 28, while venting to atmosphere through port 34. All other ports are closed during cycling. Fluid 60 travels from the upper processing chamber 14 into the lower process chamber 16 and headspace 22. By applying a pressure differential above the critical pressure for liquid flow through the porous substrate 18 while not exceeding the critical pressure required for air flow through the porous substrate 18, flow continues until all liquid 60 is drawn from the upper processing chamber 14 and then stops. This design ensures that no air is drawn through, eliminating any bubbles that might interfere with processing or operation of the cartridge.

Figure 5:
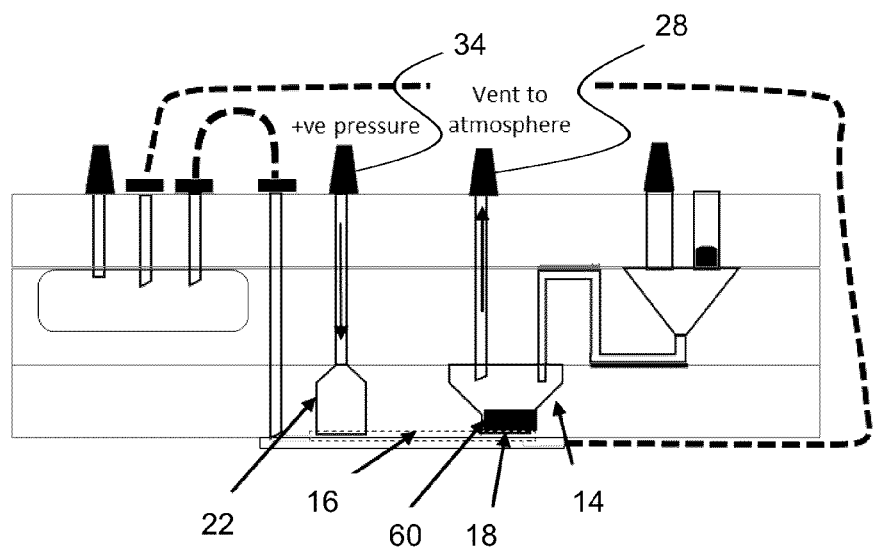
FIG. 5 shows the liquid in the cartridge being moved back into the upper processing chamber under pneumatic control.

Referring to FIG. 5, to provide repeated contact with porous substrate 18 alone or in combination with the solid support 44 and to ensure efficient mixing, fluid 60 may be returned to the upper processing chamber 14 by reversing the process. A differential pressure is created by applying pressure to port 34 while simultaneously venting to atmosphere through port 28. By applying a pressure differential above the critical pressure for liquid flow through the porous substrate 18 while not exceeding the critical pressure required for air flow through the porous substrate 18, flow continues until all liquid 60 is drawn from the lower processing chamber 16 back up to upper chamber 14 and then stops. This principle eliminates the need for any precise volumetric control of fluid flow and greatly simplifies control. The process of cycling back and forth through the substrate 18 can be repeated as many times as required.

Figure 6:
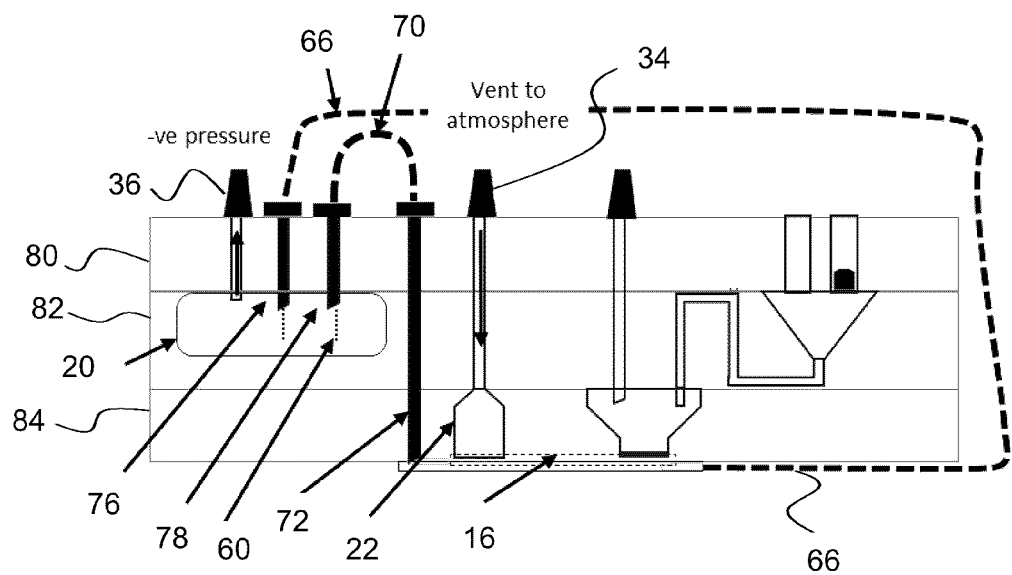
FIG. 6(a) shows the liquid in the cartridge partially moved into a waste container after completion of the processing steps.
FIG. 6(b) shows a kit including a disposable cartridge along with a dedicated blister pack containing a plurality of assay reagents and a matching gasket with the packets containing the assay reagents being aligned with preselected reagent chambers.
Figure 6:
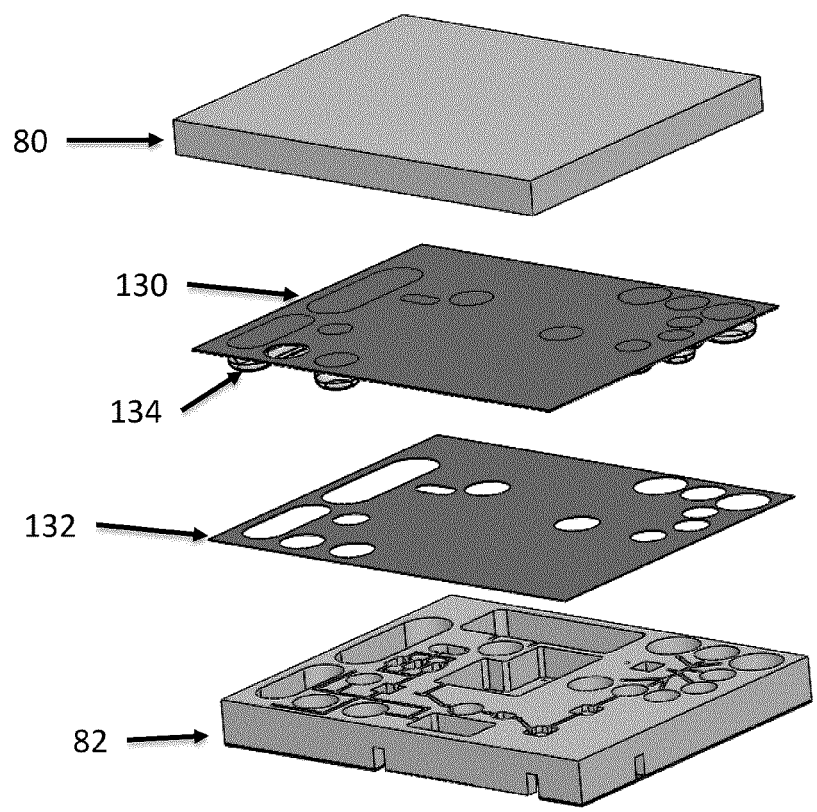
Figure 7:
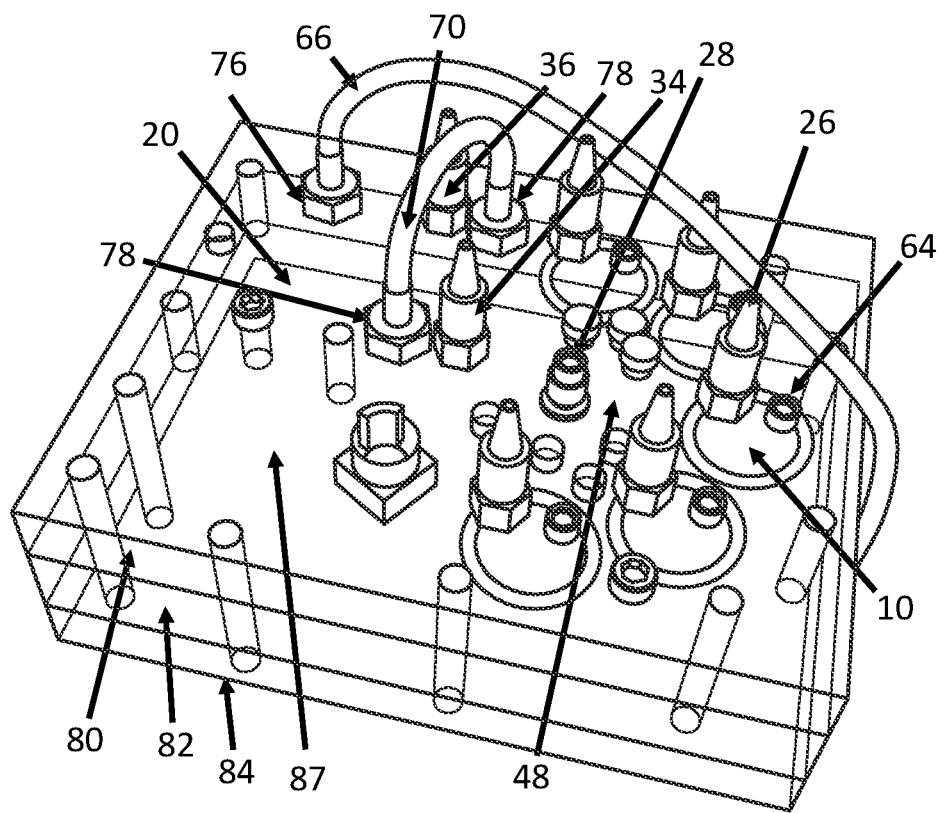
FIG. 7 is a photograph of an assembled cartridge showing five (5) reagent/sample chambers and a bulk reagent chamber connected to a central upper processing chamber.

Referring to FIG. 6(*a*), evacuation of the fluid from the lower processing chamber 16 is effected by applying a negative pressure through port 36 on chamber 20 while venting to atmosphere through port 34. This allows air to enter through the lower processing chamber 16 headspace 22 and liquid 60 to travel though a distal waste capillary channel 66 from one side of lower chamber 16 coupled to a waste inlet 76 which empties into chamber 20 and a proximal waste capillary 70 coupled to a proximal waste outlet 72 exiting from the other side of chamber 16 coupled to a waste outlet 78 which empties liquid 60 into chamber 20.

FIG. 6(*b*) shows an embodiment which is a kit including a disposable cartridge 100 along with a dedicated blister pack 130 containing a plurality of packets 134 containing selected liquid assay reagents and a matching gasket 132 with the packets 134 containing the assay reagents being aligned with preselected reagent chambers in plastic cartridge reagent plate 82. The assembled cartridge 100 with upper cartridge plate 80 includes the packets 134 partially projecting into their corresponding reagent chambers. When inserted into the instrument to implement the biological assay, applying pressure via the pneumatic system coupled to the pneumatic ports on plate 80 (not shown) of the various chambers results in rupturing of frangible seals in the blister pack resulting in the reagents flowing into their respective chambers. The gasket 132 provides a liquid and gas seal between chambers. Additional solid reagents may be deposited into preselected reagent chambers within plastic cartridge reagent plate 82 prior to assembly of cartridge 100, providing flexibility in the customization of reagent selection for desired biological assays and simplifying storage and transport requirements.

Figure 25:
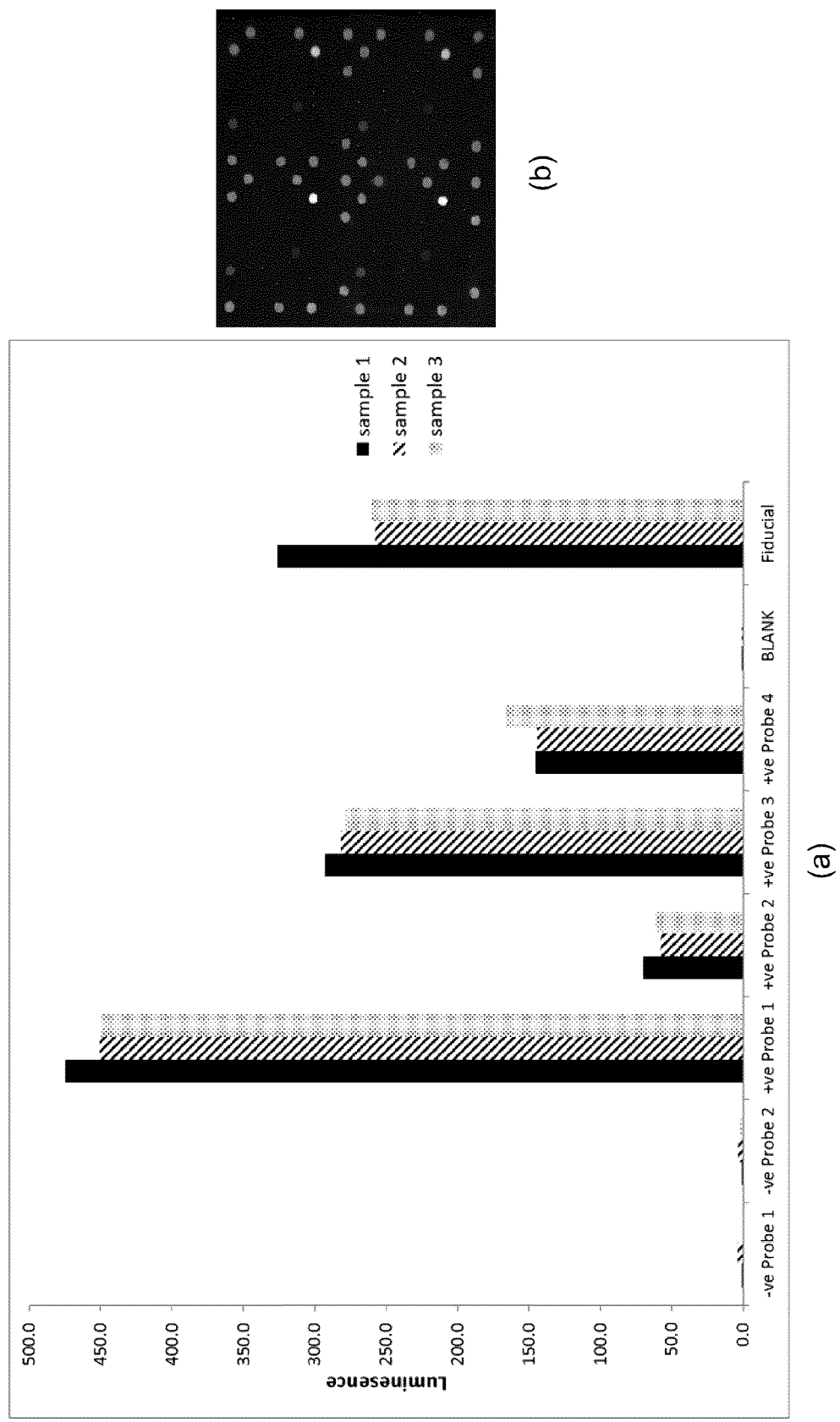
FIG. 25(a) shows results of a nucleic acid bioassay conducted using the assembled cartridge shown in FIG. 7.
FIG. 25(b) shows the chemiluminescent image of the porous substrate contained within the assembled cartridge shown in FIG. 7 at the conclusion of the nucleic acid bioassay

As noted above, FIG. 7 is a photograph of an assembled cartridge showing five (5) reagent/sample chambers 10 connected to a central upper processing chamber 14. This photograph shows the cartridge without the pneumatic connection to the cartridge. A nucleic acid bioassay (FIG. 25) and a protein bioassay (FIG. 26) were conducted using the assembled cartridge shown in FIG. 7.

Analysis of nucleic acids usually requires processing steps to isolate nucleic acids and to derive labelled copies of them for subsequent detection. Many applications require the analysis of many different target sequences, and high analytical sensitivity is often required. Furthermore, automated, cost-effective systems will be required so that relatively unskilled people will be able to perform the tests reliably for routine clinical testing.

Purification and amplification of multiple nucleic acids targets can be performed by capturing the nucleic acids on a solid support and performing a series of incubation and washing steps on the support to produce derivatives of the nucleic acids that can be analyzed by hybridization on nucleic acid probes arrayed on the porous substrate.

FIG. 8 and its included legend shows a top view of a configuration of a bioassay cartridge 200 which incorporates design of cartridge 100 but is configured for both nucleic acid sample preparation and nucleic acid amplification (isothermal or polymerase chain reaction (PCR)) and multiplex detection of the products. Cartridge 200 is configured for both sample preparation using one porous support 18 in processing chamber A 209 and reaction product detection using a second porous substrate 18 in processing chamber B 224 each consisting of an upper processing chamber 14 and a lower processing chamber 16 separated by porous substrate 18.

Cartridge 200 provides for a sample inlet 208, a means to mix the sample with a lysis or pretreatment buffer 210, a processing chamber 209 containing porous substrate 18 in which capture and modification of nucleic acids from the sample can be performed using dried or liquid reagents supplied from chambers 205, 207, 201, 202, 203, 204, or 206. Fluids from the processing chamber A 209 may be transferred to waste chamber A 226 or in the case of fluid containing the derivative nucleic acids to a thermal treatment chamber A 211 or intermediate chamber A 212.

Figure 9:
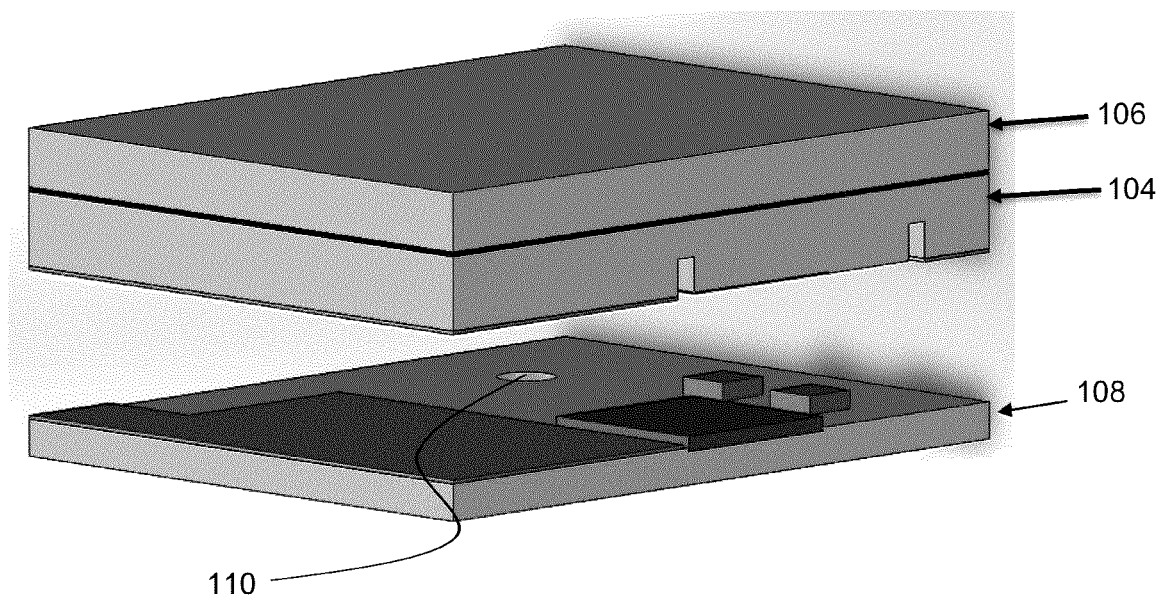
FIG. 9 shows a partially disassembled view of the disposable cartridge sandwiched between an upper pneumatic block assembly interface and a lower thermal control assembly which form part of the instrument into which the cartridge is inserted.

Chamber 212 may be used to mix the fluid with dried or liquid reagent in chamber 213. Subsequently, the fluid may be processed through one or more temperature treatment chambers 214, 216 where isothermal or thermal cycling amplification may take place. These thermal treatment chambers 211, 214, 216 are isolated from the bulk of the cartridge by thermal insulating zones 215 and controlled by the application of heat or cooling from an external thermal control assembly 108 (FIG. 9). The processed liquid containing the amplified derivative nucleic acids can then be transferred to an intermediate chamber B 218, mixed with an appropriate binding buffer 219 for hybridization to the porous substrate 18, located in sample processing chamber B 224 where the derivative nucleic acids are detected on bound nucleic acid probes immobilized in specific locations on the porous substrate 18.

A series of steps as previously described are carried out using reagents from adjacent chambers 217, 220, 222, 223, 225 with spent fluids being directed to waste chamber B 227. In all cases pneumatic pressure applied through ports located on each chamber is used to control fluid movement. As a final step, an image of the porous substrate 18 is captured with a CCD camera with integral lens 120 (FIG. 10) located below the optical window 40 (FIG. 1). This image is analyzed for intensity of light measured across the porous substrate and correlated to the specific regions known to contain the immobilized probes. This information is used to calculate the presence or absence or quantity of specific nucleic acids in the original sample.

Generally speaking, using the design principles disclosed above, cartridges may be configured to have multiple reagent/sample chambers/reservoirs, upper and lower processing chambers 14 and 16, and waste chambers 20. For example, waste chamber 20 may in fact be an intermediate chamber accepting reaction products from a first processing station including first and second upper and lower processing chambers 14 and 16 with chamber 20 forming a sample chamber for a second series of upper and lower processing chambers 14 and 16.

It will be understood that cartridge 200 may be configured with additional features to permit numerous intermediate processing steps to be carried out between the first and second set of upper and lower processing chambers 14 and 16. Non-limiting examples of these intermediate processing steps may include mixing, dilution, incubation, thermal treatment including but not limited to thermal cycling to give a few examples. Optionally cartridge 200 may include a reagent chamber 228 containing a cleansing agent selected to destroy or neutralize harmful products of the assay or sample.

The system of FIG. 8 utilizing the disposable cartridge disclosed herein is very amenable to performing the above noted nucleic acid assay such as that disclosed in United States patent Publication Serial No. XXXX, which is incorporated herein by reference in its entirety, and which is a national phase entry patent application of PCT/2016/050367 filed on Mar. 29, 2016. Thus, the present disclosure provides a cartridge which in an embodiment comprises two different porous substrates each with upper and processing chambers, one of which is a solid support for purification of multiple target nucleic acids and processing of the target nucleic acids to produce derivative nucleic acids, and the other of which is a porous substrate on which the derivative nucleic acids are detected on bound nucleic acid probes. The present cartridge, in conjunction with an instrument designed to operate it, will accept samples and provide clinically relevant information without user intervention after inserting the samples.

Analysis of proteins in biological samples (e.g., human serum) by immuno-binding reactions often requires dilution of the samples before the immuno-binding reactions. The present disclosure provides embodiments of a disposable cartridge comprising two different porous substrates 18 each with associated upper and lower processing chambers 14 and 16, one of the coupled chambers 14 and 16 may be used for mixing of the sample with a diluent, and the second of the coupled chambers 14 and 16 includes a flow-through porous substrate 18 on which the proteins are detected by immuno-binding reactions.

Specific volumes of the sample and of the diluent are transported to the upper processing chamber 14 above the first porous support 18, and they are mixed by passing the solution through the porous substrate 18 into the lower processing chamber 16, and are pneumatically cycled or driven back and forth between the chambers 14 and 16 at least one time before the diluted samples are transported from the first lower processing chamber 16 to the second buffer processing chamber 14 above the second porous substrate 18 for detection on the second porous substrate 18. The first porous substrate 18 may contain immobilized binding agents that would bind specific components in the sample. For example, interfering substances might be removed by binding to the first porous substrate 18 before the immuno-binding step on the second porous substrate 18 is performed.

In another instance, low abundance substances may be concentrated from a large volume by binding to the first porous substrate 18 and then being released in a smaller volume at higher concentration before the immuno-binding step on the second porous substrate 18 is performed in order to improve overall sensitivity of detection.

FIG. 9 shows a partially exploded view of the disposable cartridge 104 sandwiched between an upper pneumatic block assembly interface 106 and a lower thermal control assembly 108 which form part of the instrument into which the cartridge 104 is inserted. Pneumatic interface 106 includes all the requisite pneumatic coupling components, tubes and the like needed to couple to the pneumatic ports of the cartridge 104. All these components are housed in interface 106 and do not form part of the disposable cartridge 104.

Figure 10:
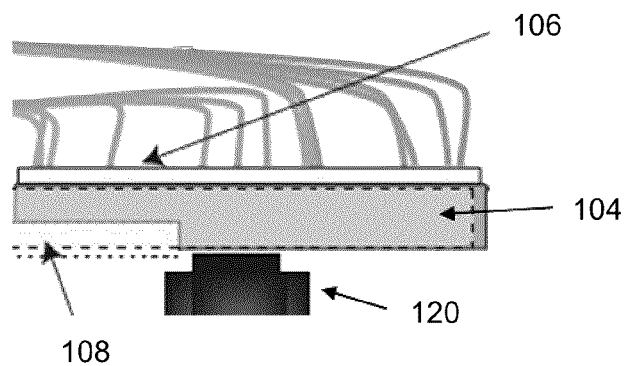
FIG. 10 is a partial cross sectional view of the sandwiched structure of FIG. 9 showing a detector positioned to view the porous substrate.
Figure 11:
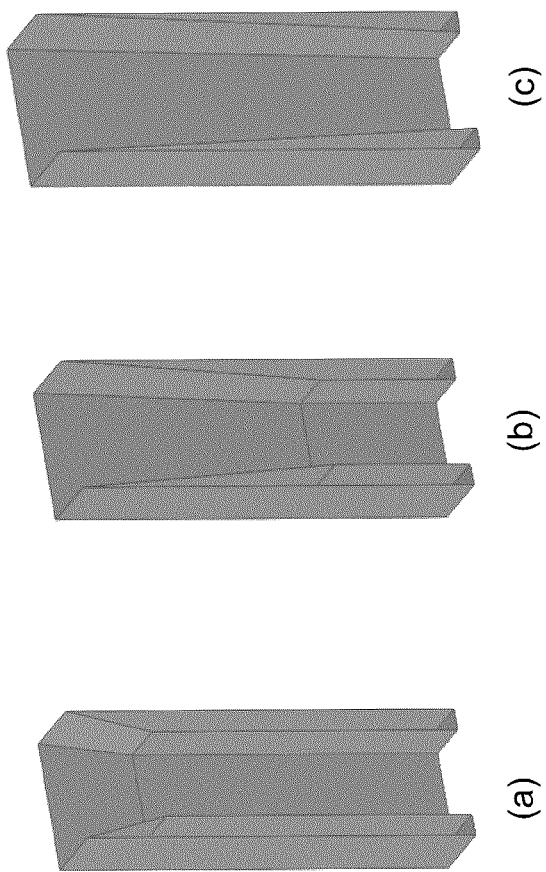
FIGS. 11(a) to 11(c) show three (3) tapered pores with different angles of tapering. Smaller tapering angle ((b) compared to (a)) leads to deeper tapering. For small enough angles the tapering is continuous from one surface of the substrate to the other as shown in (c).
Figure 13:
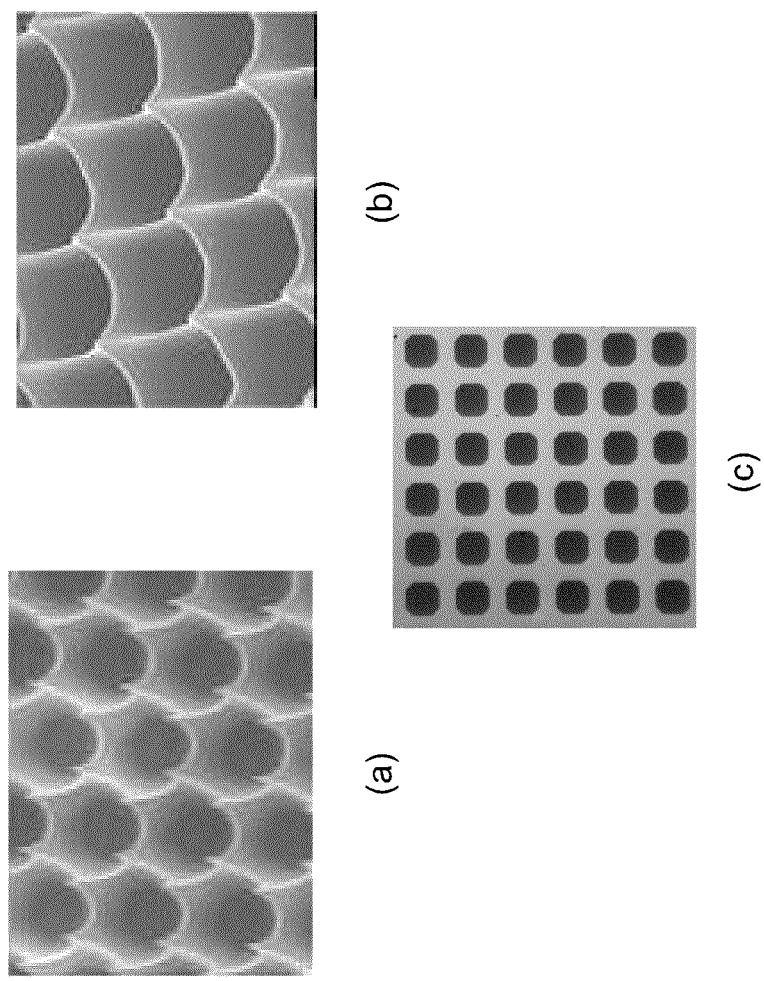
FIGS. 13(a) to 13(c) show micro photographs of the substrates with pores of a different cross section with FIG. 13(a) being circular, FIG. 13(b) being square, and FIG. 13(c) being polygonal.
Figure 14:
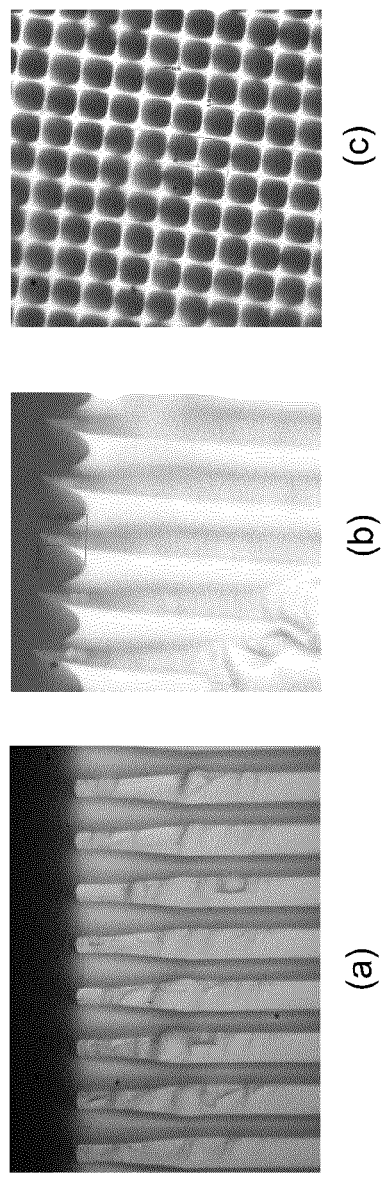
FIGS. 14(a) to 14(c) show the tapered pores with different angles of tapering and as a result with different depths of tapered portion of a pore, with the optical micrographs showing the cross sections of tapered pores with different angles of tapering 14(a), 14(b) and the top view, 14(c) of the substrate cross section of which is shown in FIG. 14(a).

Similarly, thermal control assembly 108 contains all requisite features such as heaters, temperatures sensors and associated controllers, microprocessors and the like to control the temperature in selected zones of the cartridge 104. The thermal control assembly 108 includes a central aperture 110 which when assembled with cartridge 104 aligns with optical window 40 to allow imaging of the porous substrate 18. FIG. 10 is a partial cross sectional view of the sandwiched structure of FIG. 9 showing detector 120 positioned to view this porous substrate 18 in the assembled system. Detector 120 which includes an appropriate objective lens is configured to image the bottom side of porous substrate 18 to detect the presence of colorimetric, fluorescent, chemiluminescent, or bioluminescent signals.

A preferred material from which the porous substrate 18 is produced is silicon which is rigid and opaque to chemiluminescent emission. This opacity prevents crosstalk between different pores of the substrate and hence prevents crosstalk between closely spaced regions on the substrate with different binding agents. This permits the analysis of many analytes in a small device, since different binding agents can be arranged in close proximity. As an example, the substrate may contain pores with a size in the range of 1 to 15 microns with wall thicknesses between pores ranging from 1 to 5 microns.

Referring to FIGS. 11(a) to 14(c) inclusive, in an embodiment of the porous substrate 18, the two opposed sides have different pore sizes. The side of the substrate 18 from which light is collected to enable detection and analysis has substantially wider pores as can be seen in FIGS. 11(a) to 14(c), and this side is the side facing into lower reaction chamber 16 and faces the optical window 40 from which the detector 120 (FIG. 10) is spaced. As can be appreciated from FIGS. 11(a) to (c), the walls of the pores at this surface are tapered rather than being normal to the surface. This geometry presents a greater surface area to the detection optics and less restriction to the transmission of light from within the pores. Despite the large pores on a front surface and great porosity, the substrate 18 has adequate strength and structural stability for flow-through applications due to the small pore size on the opposite side and there is a substantial amount of material between the pores.

Figure 15:
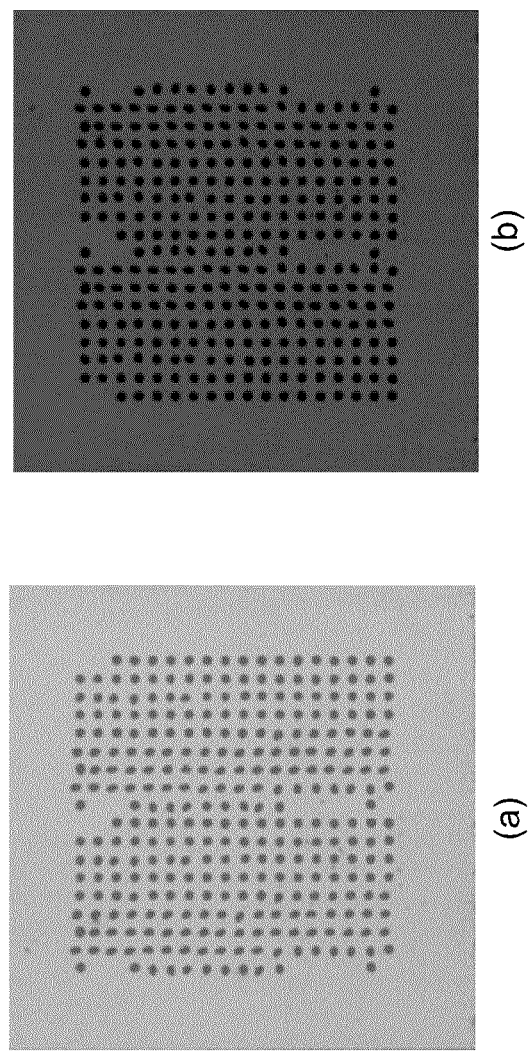
FIGS. 15(a) and 15(b) demonstrate the improvement in light transmission of a porous substrate due to pore tapering. The same substrate is shown in FIGS. 15(a) and 15(b) when illuminated by the same diffuse light source. The widened part of the pores are facing the objective lens in FIG. 15(a), and the narrow part of pores are facing the objective lens in FIG. 15(b). The spots on the substrates are regions in which the pores of the substrate have been blocked with probe solutions that have dried in the pores.

The remarkable asymmetric optical properties of the substrate are illustrated in FIGS. 15(a) and (b). Specifically, FIGS. 15(a) and 15(b) demonstrate the improvement in light transmission of a porous substrate due to pore tapering. The same substrate is shown in 15(a) and 15(b) when illuminated by the same diffuse light source. The widened part of the pores are facing the objective lens in FIG. 15(a) and the narrow part of the pores are facing the objective lens in FIG. 15(b). The spots on the substrates are regions in which the pores of the substrate have been blocked with probe solutions that have dried in the pores.

Figure 16:
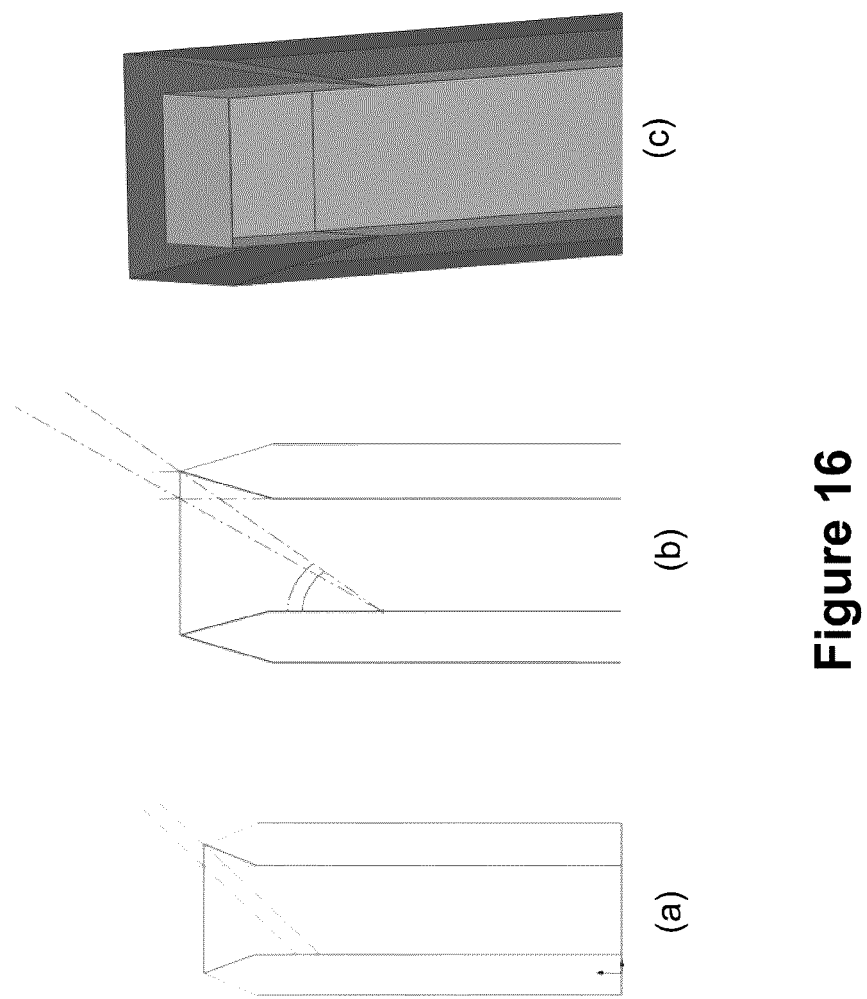
FIGS. 16(a) to 16(c) illustrate the mechanisms contributing to light collection improvement, with 16(a) showing the effect of increasing of the effective depth; 16(b) showing the effect of an increase in the collection angle; and 16(c) showing the effect of increase of surface area.

Tapering of the pore walls provides improvement of light collection due to increase of the depth from which the light can be collected, increase of the emitting surface area of the upper portion of a pore and increase of a collection angle. These mechanisms of light collection efficiency are illustrated in FIGS. 16(a) to 16(c) with 16(a) showing the effect of increasing of the effective depth; 16(b) showing the effect of an increase in the collection angle; and 16(c) showing the effect of increase of surface area.

Figure 17:
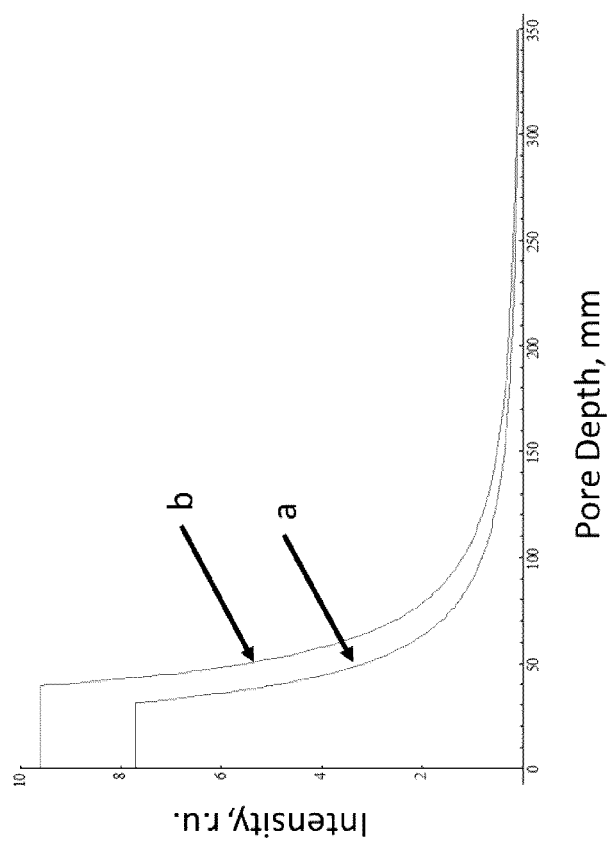
FIG. 17 shows the results of calculation of light collection efficiency as a function of pore depth for a straight 8 um (micrometers) pore (plot (a)) and a pore with tapered walls (plot (b)).

The results of the evaluation of these effects for a particular implementation of the method described in this application are shown in FIG. 17 which shows the results of calculation of light collection efficiency as a function of pore depth for a straight 8 um pore (plot (a)) and a pore with tapered walls (plot (b)). The parameters used for this evaluation are: 1) the width of non-tapered portion of a pore is 8 um; 2) the thickness of a wall between pores is 4 um; 3) the substrate thickness is 350 um; 4) tapering angle 2 degrees; 5) the diameter of the objective lens is 25.4 mm; and 6) the working distance of the objective lens is 50 mm.

In FIG. 17 the rise of the flat part of the curve is caused by increase of the collection surface area, the shift of the curve is caused by increase of the pore depth from which the light collection is limited by the parameters of the optical assembly rather than the pore walls, the change in a slope of the curve is associated with a change of the collection angle. As a result, the expected improvement of light collection efficiency is 1.4 to 1.5 fold.

Figure 18:
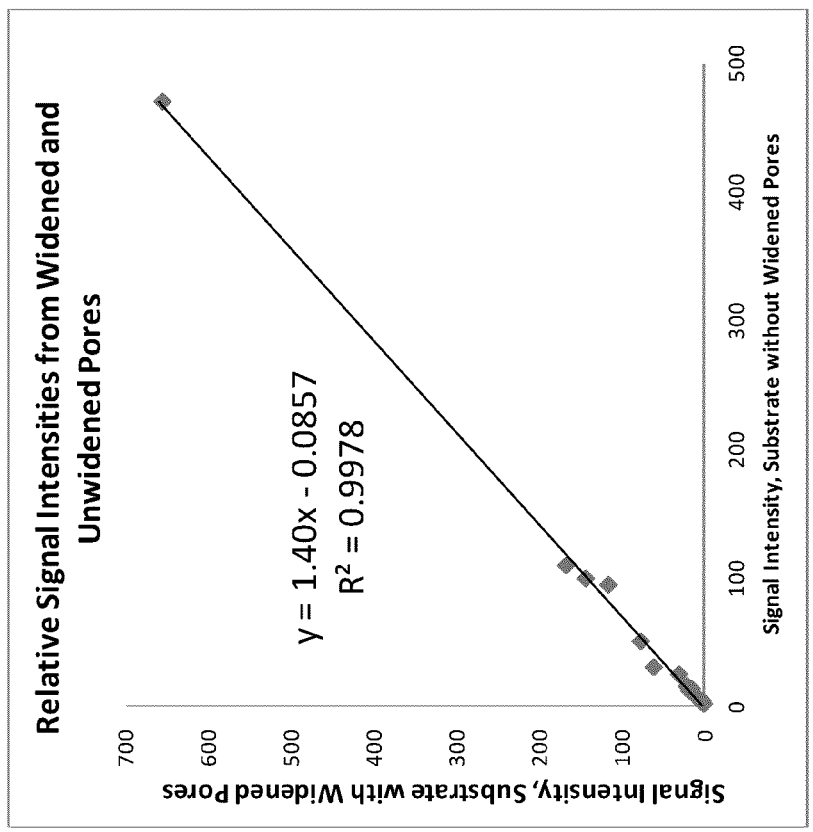
FIG. 18 shows the results of experimental comparison of signal intensities measured with a substrate with straight pores and with tapered pores.

The substrate 18 using silicon has been used to manufacture flow-through chips on which different probes have been immobilized in discrete regions or spots. The same flow-through chips have been manufactured with a highly porous silicon substrate with pore walls normal to the surface. When these flow-through chips were hybridized with the same target molecules and processed with identical protocols to detect chemiluminescent labels attached to target molecules bound by the probes, the signal intensities were approximately 40% greater with the substrate described in this invention (FIG. 18). This experimental result confirms the theoretical evaluation of efficiency enhancement due to pore tapering. The enhanced optical detection sensitivity improves the sensitivity of assays performed on the chips and/or improves the throughput of the assay system.

The suggested approach is not very sensitive to a particular selection of the tapering angle as long as the inner plane of a pore wall does not restrict light collection. For the parameters listed above the tapering angle can be selected in the range between 0.3 degrees (tapering of a pore wall along full pore depth) to approximately 14 degrees. Tapering with the angles outside of this range will still increase amount of collected light, but the improvement will be less pronounced. It is noted that selection of a particular tapering angle and depth of tapering can be additionally influenced by the process of substrate manufacturing, the selected pore size and membrane thickness.

Figure 19:
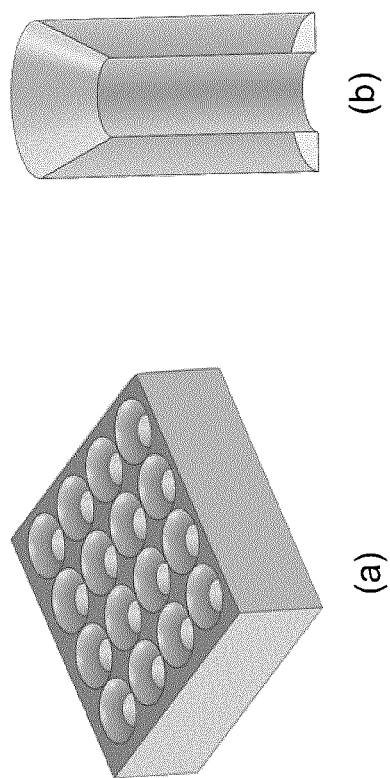
FIG. 19(a) shows another embodiment of the flow-through chip substrate with cylindrical pores with conical tapering.
FIG. 19(b) shows a section of a single pore of the embodiment of FIG. 19(a).
Figure 20:
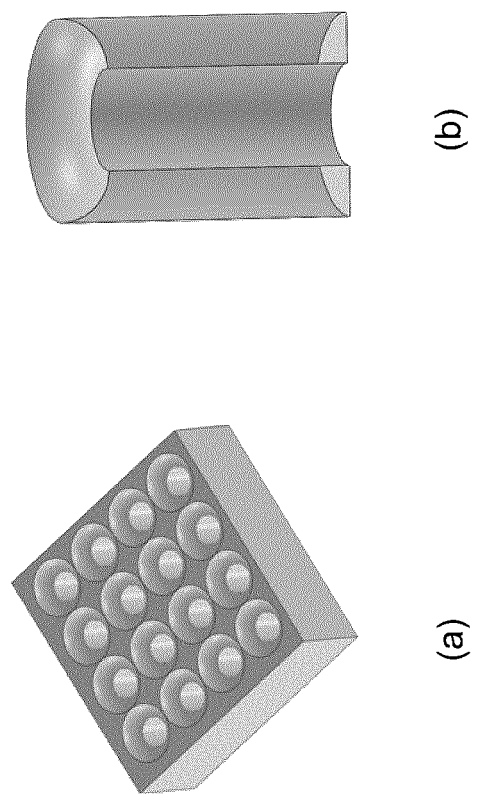
FIG. 20(a) shows another embodiment of the flow-through chip substrate with cylindrical pores with spherical tapering.
FIG. 20(b) shows a section of a single pore of the embodiment of FIG. 20(a).
Figure 21:
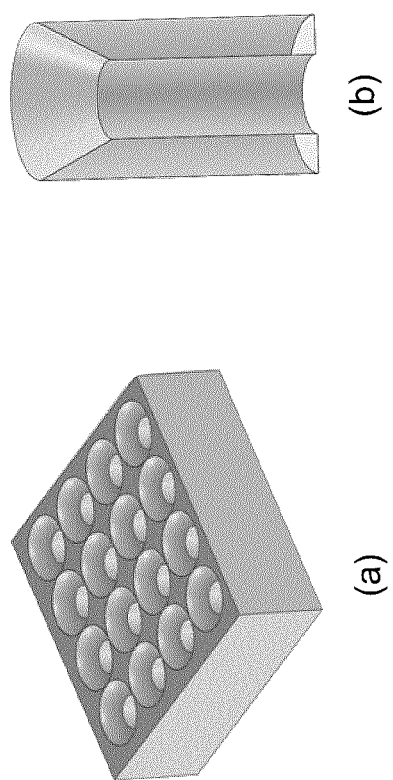
FIG. 21(a) shows another embodiment of the flow-through chip substrate with cylindrical pores with parabolic tapering.
FIG. 21(b) shows a section of a single pore of the embodiment of FIG. 21(a).

The geometry of pores does not need to be square. If the manufacturing process requires they may have a different cross section, for example, circular. In this case the pore is cylindrical (see FIGS. 19(a), 19(b) to 21(a), 21(b) inclusive). In this case the simplest form of tapering is conical as shown in FIGS. 19(a) and 19(b). The light collection efficiency can be additionally increased by changing shape of tapering from conical to spherical (see FIGS. 20(a) and 20(b)) or parabolic (FIGS. 21(a) and 21(b)).

Figure 22:
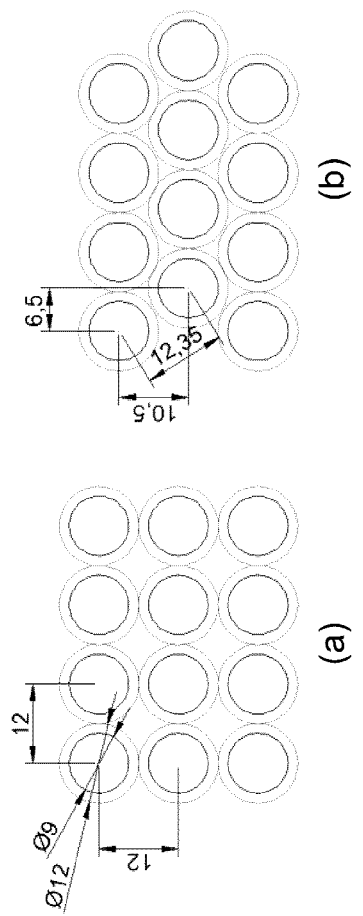
FIG. 22(a) shows a first embodiment of an arrangement of the tapered cylindrical pores in the porous substrate.
FIG. 22(b) shows a second embodiment of tapered cylindrical pores in the porous substrate being more closely packed than the arrangement of FIG. 22(a) with enhanced light collection efficiency.

Pores of different cross section (circular, square, polygonal) were derived to practice: the micro photographs of such silicon substrates are shown in FIGS. 13(a) to 13(c). The light collection efficiency can be additionally improved for a substrate with cylindrical pores by a denser arrangement of pores as shown in FIG. 22(b) compared to the collection efficiency of the packed structure of FIG. 22(a).

Figure 24:
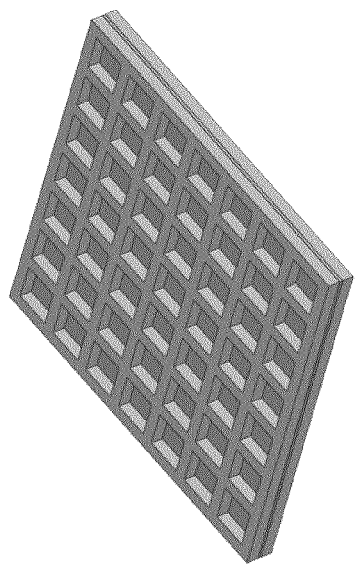
FIG. 24 shows another embodiment of a flow-through chip substrate for improved optical detection sensitivity with a high-efficiency porous substrate reinforced by two frames placed on the opposite sides of the substrate for structural stability.

The structural stability of the substrate material depends on the type of material (e.g. silicon or plastic) and its thickness. If the substrate is thin or/and the material is flexible or soft, a reinforcement frame can be used to strengthen the substrate (see FIGS. 23 and 24). The substrate can be attached to a single frame (see FIG. 23) or, preferably sandwiched between two frames (see FIG. 24) to allow bidirectional application of pressure required to drive fluids through the porous substrate as described above without damaging of the substrate.

in conclusion, the present disclosure provides a disposable sample handling cartridge for performing multiplex biological assays in which the cartridge is designed and configured to provide complex fluid processing without the need for active pumping and valving. The cartridge is readily produced using standard molding techniques, no nanostructrures are required and no precise tolerances are required. The movement of sample and reagent fluid is solely determined by application of differential pressures, which are correlated primarily with the properties of the sample substrate 18, namely pore size and distribution in the substrate 18, as well as the inner diameter of the capillary channels (e.g. 48). The cartridge disclosed herein advantageously contains no moving parts and is made of a small number of parts compared to current systems, which typically contain active pumps, active valves and the like.

The cartridge disclosed herein may be used for, but is not limited to use in sandwich, or competitive immunoassay for protein antigen analysis; serology for antibody binding to immobilized antigens for allergy, autoimmune, infectious disease; nucleic acids measurement of DNA, RNA, mRNA, microRNA (miRNA) etc. to identify specific sequences whose presence or expression is correlated to presence or progress of disease, sequences that can be used to identify species of bacteria, fungi, viruses in a sample, sequences that indicated the presence of specific resistance genes in pathogens, measurement of copy number variations (CNV's) or specific gene variants or deletions that correlate to risk of disease, gene signatures used to type samples for forensic or identification purposes. In addition, it may be used for small molecule measurements including drugs and environmental contaminants. It may also be used in multiple sample matrices including human and animal fluids and tissues, food and agricultural samples, environmental samples, cells and lysates of cells, and bioprocessing fluids.

Non-limiting exemplary uses of the disposable cartridge disclosed herein will now be given using a nucleic acid assay and a protein assay.

Examples

FIG. 25(a) shows results of a nucleic acid bioassay wherein a sample containing biotin labelled PCR products representing copies of specific gene sequences from bacterial samples were processed using the cartridge shown in FIG. 7. Prior to assembly of the cartridge, the porous substrate 18 was functionalized in discrete regions to form analysis spots, each of approximately 200 um in diameter, with oligonucleotide probes containing sequences complementary to sequences known to occur in the amplified bacterial gene (+ve Probes 1, 2, 3, 4), sequences not known to occur in the amplified bacterial gene (−ve Probes 1, 2) or a sequence complementary to an artificial oligonucleotide added to the sample (Fiducial). In addition, one blank spot where no oligonucleotide probe was immobilized was used as a control to measure background signal. 5 individual reagent wells 10 and a bulk chamber 87 were used.

The reagent chambers were individually loaded with blocking buffer, hybridization buffer, sample, streptavidin-HRP and chemiluminescent substrate respectively. The bulk reservoir 87 was loaded with wash buffer. Reagents were transferred to the upper processing chamber in individual steps as illustrated in FIG. 3. Each liquid was then transferred to the lower processing chamber as illustrated in FIG. 4 and then returned to the upper processing chamber as illustrated in FIG. 5.

After repeating this cycle back and forth through the porous substrate 18 as many times as required for each step the reagent was removed to waste chamber as illustrated in FIG. 6. Between each step an aliquot of wash buffer from bulk chamber 87 was similarly processed. The sequential steps accomplished blocking of the porous substrate to prevent non-specific binding, hybridization of PCR products in the sample to the probes containing complementary sequences immobilized in discrete regions on porous substrate 18, binding of streptavidin-HRP to the biotin label on captured PCR products, and introduction of a chemiluminescent substrate that could be processed by the captured HRP enzyme to produce a chemiluminescent emission in that specific region.

During the final step, an image of the porous substrate 18 was captured with a CCD camera 120 located below the optical window 40. This image FIG. 25(b) was analyzed for intensity of light measured across the porous substrate 18 and correlated to the specific regions known to contain the immobilized probes. FIG. 25(a) shows the luminescent intensity for three repeats of the bioassay for the same sample. It will be noted that significant signals are observed on analysis spots formed by immobilizing probes containing complementary sequences to gene sequences expected in the sample (+ve Probes 1, 2, 3, 4), minimal signal is observed on analysis spots formed by immobilizing probes containing complementary sequences to gene sequences not expected in the sample (−ve Probes 1, 2). As expected, no signal was observed on the blank analysis spot, and substantial signal was observed on the analysis spot containing a complementary sequence to the artificial oligonucleotide added to the sample prior to analysis.

Figure 26:
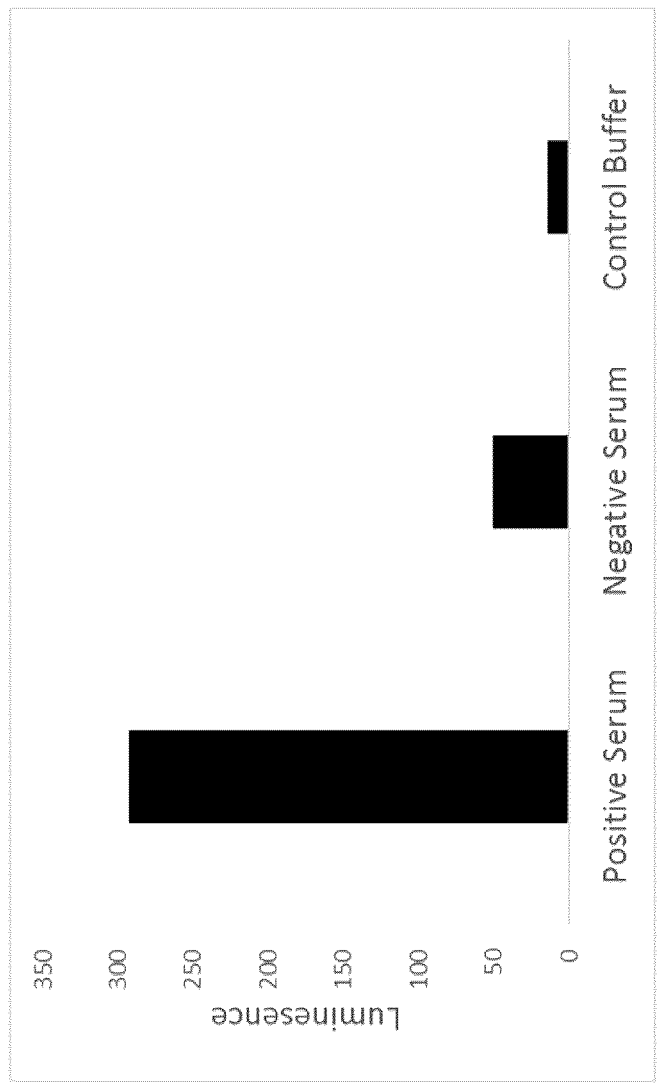
FIG. 26 shows results of a protein bioassay conducted using the assembled cartridge shown in FIG. 7.

FIG. 26 shows results of protein bioassays on human serum or control buffer to determine the presence of antibodies against the measles virus carried out using the cartridge pictured in FIG. 7. Prior to assembly of the cartridge, the porous substrate 18 was functionalized in discrete regions to form analysis spots, each of approximately 200 um in diameter, with a deactivated measles virus preparation. Four reagent chambers were individually loaded with blocking buffer, sample, HRP labelled anti human immunoglobulin G and chemiluminescent substrate, respectively. The bulk reservoir 87 was loaded with wash buffer.

Reagents were transferred to the upper processing chamber in individual steps as illustrated in FIG. 3. Each liquid was then transferred to the lower processing chamber as illustrated in FIG. 4 and then returned to the upper processing chamber as illustrated in FIG. 5. After repeating this cycle back and forth through the porous substrate 18 as many times as required for each step the reagent was removed to waste chamber as illustrated in FIG. 6. Between each step an aliquot of wash buffer from bulk chamber 87 was similarly processed. The sequential steps accomplished blocking of the porous substrate to prevent non-specific binding, binding from the sample of any immunoglobulins containing regions that are specific to components of the measles virus immobilized in discrete regions on porous substrate 18, binding of anti-human immunoglobulin G antibody coupled to a HRP enzyme to any retained anti-measles immunoglobulins, and introduction of a chemiluminescent substrate that could be processed by the bound HRP enzyme to produce a chemiluminescent emission in that specific region.

During the final step, an image of the porous substrate 18 was captured with a CCD camera 120 located below the optical window 40. This image was analyzed for intensity of light measured across the porous substrate 18 and correlated to the specific regions known to contain the immobilized virus. The chart in FIG. 26 shows the luminescence intensity recorded for three types of samples. It will be noted that significant signal corresponding to the presence of measles specific antibodies is observed from the serum sample drawn from a patient known to have immunity to the measles virus (positive serum). Significantly lower signal is observed from serum drawn from a patient known to have reduced immunity to the measles virus (negative serum). Minimal signal is observed from a control buffer sample that does not contain any measles specific antibodies.

Figure 27:
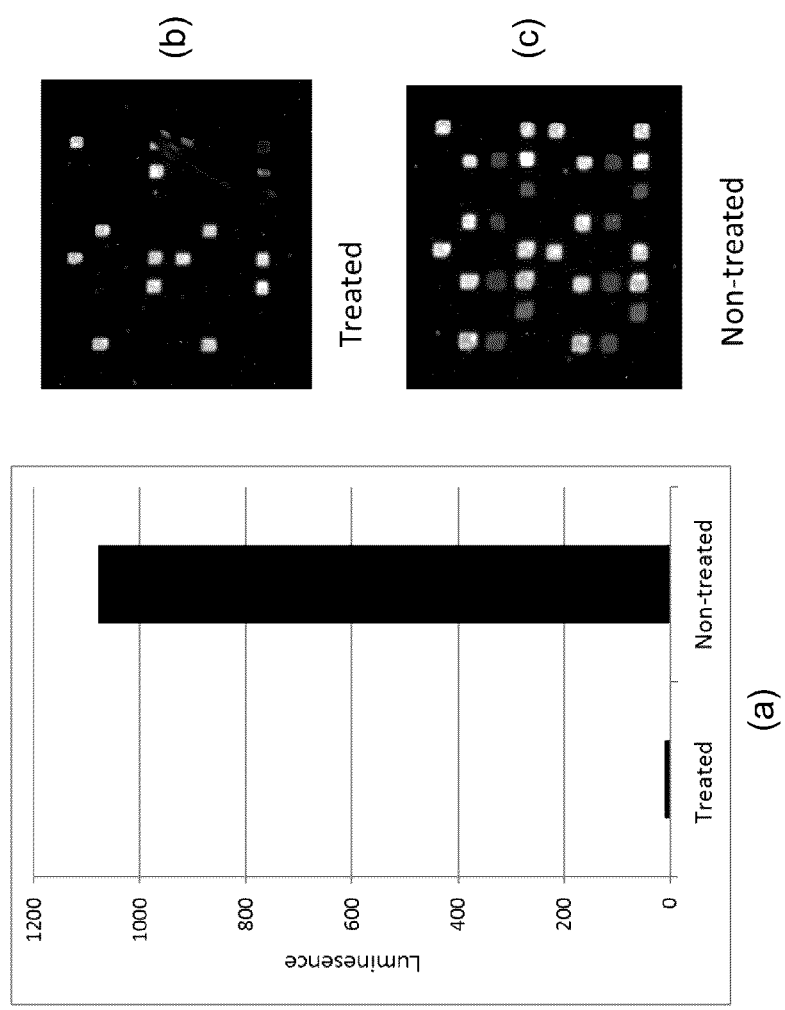
FIG. 27(a) shows results of a sample preparation using a porous substrate forming part of the present cartridge.
FIG. 27(b) shows the chemiluminescent image of a porous substrate used to detect residual protein analytes in a solution processed by a separate porous substrate configured for sample preparation.
FIG. 27(c) shows the chemiluminescent image of a porous substrate used to detect residual protein analytes in a solution prior to processing by a separate porous substrate configured for sample preparation.

FIG. 27(a) illustrates the results of a process that utilizes two different porous substrates each with upper and processing chambers, one of which is a solid support for capture of protein analytes, and the other of which is a porous substrate on which the protein analytes are detected on bound protein specific receptors. In this example, identical samples containing biotinylated mouse IgG analyte were cycled through a porous substrate 18 that was functionalized with a rabbit anti-mouse antibody know to have a high binding affinity for mouse IgG (Treated sample) or cycled through a porous substrate 18 that had not been functionalized, (Non-treated sample).

The resulting fluid was then processed through a porous substrate that had been functionalized in discrete regions to form analysis spots, each of approximately 200 um in diameter with either a rabbit anti-mouse antibody known to have a high binding affinity for mouse IgG or a biotinylated bovine serum albumin to serve as a reference spot. Washing, binding of streptavidin-HRP to any captured biotin-mouse IgG and immobilized biotin-BSA, and introduction of a chemiluminescent substrate that could be processed by the bound HRP enzyme to produce a chemiluminescent emission in that specific region were sequentially carried out. During the final step, an image of the porous substrate 18 was captured with a CCD camera 120 located below the optical window 40. The intensity of each spot functionalized with rabbit anti-mouse IgG correlates with the amount of biotinylated mouse IgG analyte present in the solution.

FIG. 27(a) shows that the sample that had been processed by the first functionalized porous substrate 18 (Treated) was almost completely depleted of mouse IgG analyte when processed on the second porous substrate 18 used for detection. It can also be observed that the sample that had been processed by the first non-functionalized porous substrate 18 (Non-treated) exhibited high levels of mouse IgG analyte when processed on the second porous substrate 18 used for detection.

FIG. 27(b) represents the signal captured by the CCD camera 120 from the second porous substrate 18 for the treated sample. Significant signal is observed only on the reference biotinylated BSA analysis spots. FIG. 27(c) represents the signal captured by the CCD camera 120 from the second porous substrate 18 for the non-treated sample. Significant signal from the analysis spots for both the reference biotinylated BSA and the biotinylated mouse IgG can be observed. This illustrates the high efficiency of using a first porous substrate 18 functionalized with analyte specific reagents to deplete those analytes prior to detection and quantitation on a second porous substrate 18. As an example, this may have utility in removing or depleting substances that may interfere with analysis on the second porous substrate 18.

Therefore what is claimed is:

1. A disposable sample handling cartridge for performing multiplex biological assays, comprising:
    a) a processing chamber including
        an upper processing chamber having a preselected volume and having a pneumatic port mounted on a top of the upper processing chamber;
        a lower processing chamber, said upper processing chamber being located on top of said lower processing chamber, and including a pneumatic port mounted on a top of the lower processing chamber;
    b) a porous substrate positioned to separate the upper processing chamber from the bottom processing chamber with the porous substrate forming the bottom of the upper processing chamber wherein the porous substrate is connected to a body of the upper processing chamber in such a way that fluids can only exit through the bottom of the upper processing chamber into lower processing chamber by passing through the porous substrate when an applied pressure differential across the porous substrate exceeds a critical pressure, said porous substrate projecting down into said lower processing chamber to form at least one head space in the lower processing chamber adjacent to the side of the portion of the porous substrate projecting into the lower processing chamber;
    c) one or more reagent chambers being in flow communication with said upper processing chamber by capillary channels configured to terminate in a top of the upper processing chamber such that they are located above a level of liquid in the upper processing chamber while performing assays, each of said one or more reagent chambers including at least one pneumatic port located on a top of each of said one or more reagent chambers, a volume of the upper processing chamber being selected to be greater than a liquid volume provided by the one or more reagent chambers to provide a head space in an upper portion of the upper processing chamber into which the capillary channels terminate;

d) an additional chamber in flow communication with said lower processing chamber by a capillary channel terminating in a top of the additional chamber, said additional chamber including a pneumatic port mounted on a top of the additional chamber; and e) wherein transport of liquids between said one or more reagent chambers, processing chambers and said additional chamber are controlled by application of pneumatic pressures with magnitudes required to overcome capillary pressure resistance between said one or more reagent chambers, processing chambers and said additional chamber.

2. The cartridge according to claim 1 wherein said porous substrate has a plurality of pores with a cross section and size of individual pores configured to provide flow resistance at liquid-gas interfaces to provide control of flow of liquid through the porous substrate and block flow of gas bubbles through the porous substrate.

3. The cartridge according to claim 2 wherein the porosity of said porous substrate and the thickness of said porous substrate is selected to provide a required flow rate for a selected range of differential pressure.

4. The cartridge according to claim 1 wherein the porous substrate is a generally planar porous substrate material having opposed surfaces and pores extending through a thickness of said porous substrate in which the pores have a greater width near a surface of the substrate facing into the lower processing chamber compared to a width of the pores on the opposed surface facing into the upper processing chamber, thereby improving a collection efficiency of light emitted from light emitting constituents from within the pores.

5. The cartridge according to claim 4 in which the pores are progressively wider near one surface of the substrate.

6. The cartridge according to claim 4 in which the pores have a rectangular cross section.

7. The cartridge according to claim 4 in which the pores have a square cross section.

8. The cartridge according to claim 4 in which the pores have a circular cross section.

9. The cartridge according to claim 1 wherein said lower processing chamber includes an optical window along a bottom wall of said lower processing chamber for permitting light to enter and exit said lower processing chamber, said optical window is spaced from a bottom planar surface of said porous substrate defining a constant gap therebetween, said bottom planar surface being viewable by a detection device spaced from said optical window for detecting optical emissions from said porous substrate.

10. The cartridge according to claim 1 wherein said porous substrate is functionalized with binding substances bound in pores of the porous substrate selected to interact with preselected analyte species in the liquid.

11. The cartridge according to claim 1 wherein said porous substrate includes organized patterns of different analyte-specific binding agents bound in different regions of the bottom planar surface of the porous substrate.

12. The cartridge according to claim 7 wherein said different binding agents are contained within the interior surfaces of the widened pores and they, or materials specifically bound to them, emit light, the optical characteristics of which may be different for said different binding agents.

13. The cartridge according to claim 1 configured to include one or more thermally isolated regions which can be heated or cooled independently of the rest of the cartridge.

14. The cartridge according to claim 1 wherein said porous substrate is a rigid porous substrate.

15. The cartridge according to claim 10 wherein said rigid porous substrate is a porous silicon dioxide substrate.

16. The cartridge according to claim 1 wherein at least one of said capillary channels that terminate at the top of the upper processing chamber and at the top of the additional chamber has a tapered capillary end portion to effect complete transfer of the reagent to the upper processing chamber with minimal carryover of the reagent to the upper processing chamber in subsequent steps of the assay process.

17. The cartridge according to claim 1 wherein said capillary channels that terminate at the top of the upper processing chamber and at the top of the additional chamber have end portions that are spaced away from side walls of the chambers.

18. The cartridge according to claim 1 further comprising a blister pack containing pre-selected reagents, the blister pack being configured to have a pre-selected number of individual packets which, when assembled with the cartridge, are aligned with pre-selected chambers and project partially into said chambers.

19. The cartridge according to claim 14 including a gasket having a shape configured to mate with the blister pack and the cartridge so that when the blister pack and cartridge are assembled the gasket forms liquid and air seals between chambers in the cartridge.

20. The cartridge according to claim 14 wherein each individual packet includes a frangible seal having a strength selected such that upon applying pressure to the different chambers via the pneumatic system coupled to the pneumatic ports of the different chambers results in rupturing of said frangible seals in the blister pack resulting in the reagents flowing into their respective chambers.

21. The cartridge according to claim 1 wherein said pneumatic ports associated with said upper processing chamber and said lower processing chamber are configured to switch between positive and negative differential pneumatic pressures in order to cycle liquid back and forth between said upper and lower processing chambers.

22. The cartridge according to claim 1 wherein said additional chamber in flow communication with said lower processing chamber is a waste container into which waste reagent and sample liquids are routed.

23. The cartridge according to claim 1 including a plurality of additional processing chambers each having paired upper processing chambers on top of lower processing chambers with each pair being separated by an associated porous substrate, each additional paired upper and lower processing chambers having associated pneumatic ports, and each additional upper processing chamber optionally being in flow communication with said one or more reagent chambers by capillary channels terminating in a top of the upper chamber, and wherein said lower processing chambers are in flow communication with at one or more waste containers into which waste reagent and sample liquids are routed.

24. The cartridge according to claim 20 including one or more reagent chambers in flow communication with one or more of the upper processing chambers, lower processing chambers or the one or more waste chambers which contain a cleansing agent selected to destroy or neutralize harmful products of the assay or sample.

25. The cartridge according to claim 1 including one or more incubation chambers in flow communication with said lower processing chamber and said upper processing chamber located downstream of the lower processing chamber.

26. The cartridge according to claim 1 including flexible diaphragms present in series in at least one pneumatic port which by deformation of the diaphragms by pneumatic pressure allow effective passage of fluid volumes at least as great as the volume of liquid that is to be transported within the cartridge, but which do not allow the actual transport of substances into or out of the cartridge.

27. The cartridge according to claim 1 configured such that a pressure difference greater than the critical capillary pressure of the pores of the porous substrate may be applied to effect complete removal of liquid from the pores of the substrate.

28. The cartridge according to claim 1 in which at least one of the chambers in the device contains a dried reagent, and the dried reagent is dissolved by transferring a fluid to said chamber from another chamber in the device.

29. The cartridge according to claim 1 in which at least one of the chambers in the device contains a dried reagent, and the dried reagent is dissolved by transferring a fluid delivered to said chamber by a blister pack.

30. The cartridge according to claim 1 configured to be interfaced to an instrument, said instrument configured for supplying differential pressure to all pneumatic ports of the cartridge, temperature control of the cartridge, and means for detecting light emitted from the cartridge.

31. The cartridge according to claim 1 including an incubation chamber in in capillary flow communication with one or both of the upper reaction chamber and lower reaction chamber which the temperature is varied in a programmed manner to effect amplification of a polymerase chain reaction.

32. The cartridge according claim 1 in which reagents may be transported from said one or more reagent chambers to the upper chamber of an associated set of paired upper and lower processing chambers so that analyte molecules are modified and/or copied and in which the reagents may be removed from the lower chamber of the first set of paired upper and lower processing chambers after such reactions.

33. The cartridge according to claim 1 in which enzymes or catalysts are immobilized on said porous substrate separating an upper processing chamber located above a lower processing chamber to modify substances in the liquid transported through the substrate.

34. The cartridge according to claim 1 where a common pressure range can be used to overcome the critical pressure required to induce flow through a porous substrate separating an upper processing chamber located above a lower processing chamber and any of the capillary channels connecting chambers in the device.

35. A method for a performing biological assay, comprising: providing the disposable sample handling cartridge of claim 1; wherein the porous substrate being constructed of material containing pores selected to provide a uniform resistance to flow across its entire surface such that at a defined pressure differential across the porous substrate, liquids will pass through the pores but gases will not, the porous substrate having analyte specific receptors bound in said pores;
   applying a differential pressure between the one or more reagent chambers and a sample chamber containing an analyte and the upper processing chamber for moving liquids containing reagents from one or more reagent chambers and sample chamber through capillary channels to the upper processing chamber;
   applying a differential pressure between the upper processing chamber and the lower processing chamber for moving the liquids through the porous substrate from the upper processing chamber to the lower processing chamber with the differential pressure being selected to force the liquid through the porous substrate but not gas;
   applying a differential pressure between the lower processing chamber and a waste chamber for moving liquids from the lower processing chamber to the waste chamber;
   detecting for analytes bound to the analyte specific receptors on the porous substrate.

36. The method according to claim 35 wherein the biological assay is a nucleic acid assay.

37. The method according to claim 35 wherein the biological assay is a protein assay.

* * * * *